(12) United States Patent
Castelhano et al.

(10) Patent No.: US 6,376,667 B1
(45) Date of Patent: Apr. 23, 2002

(54) SOLID PHASE SYNTHESIS OF HETEROCYCLES

(75) Inventors: Arlindo L. Castelhano, New City, NY (US); Hui Shao, North Arlington, NJ (US)

(73) Assignee: OSI Pharmaceuticals, Inc., Uniondale, NY (US)

( * ) Notice: Subject to any disclaimer, the term of this patent is extended or adjusted under 35 U.S.C. 154(b) by 0 days.

(21) Appl. No.: 09/198,697

(22) Filed: Nov. 24, 1998

Related U.S. Application Data

(60) Provisional application No. 60/066,878, filed on Nov. 26, 1997.

(51) Int. Cl.$^7$ ............................................. C07D 239/54
(52) U.S. Cl. ........................ 544/309; 544/285; 544/278; 544/279; 544/280; 544/255; 544/256; 544/254
(58) Field of Search ................................ 544/309, 285, 544/278, 279, 280, 255, 256, 254

(56) References Cited

FOREIGN PATENT DOCUMENTS

WO          WO 94/08711          4/1994

OTHER PUBLICATIONS

F. Balkenhohl et al., Combinatorial Synthesis of Small Organic Molecules, *Angew. Chem. Int. Ed. Engl.* 1996, 35, 2288–2337.
J.S. Fruchtel et al., Organic Chemistry on Solid Supports, *Angew. Chem. Int. Ed. Engl.* 1996 35, 17–42.
P.H.H. Hermkens et al., Solid–Phase Organic Reactions: A Review of the Recent Literature, *Tetrahedron* 1996, 52, 4527.
M. J. Plunkett et al., Solid–Phase Synthesis of Structurally Divers 1,4–Benzoidiazepine Derivatives Using the Stille Coupling Reaction, *J. Am. Chem. Soc.* 1995, 117, 3306–3307.
M.M. Murphy et al., Combinatorial Organic Synthesis of Highly Functionalized Pyrrolidines; Identification of a Potent Angiotensin Converting Enzyme Inibitor from a Mercaptoacyl Proline Library, *J. Am. Chem. Soc.* 1995, 117, 7029–7030.
M. Patek et al. Solid–Phase Synthesis of "Small" Organic Molecules Based on Thiazolidine Scaffold, *Tetrahedron Lett.* 1995, 36, 2227–2230.
F. Russo et al., Pyrimido[5,4–b]indole Derivatives. 1. A New Class of Potent and Selective $\alpha_1$ Adrenoceptor Ligands, *J. Med. Chem.* 1991, 34, 1850.
D.W. Fry et al., A Specific Inhibitor of the Epidermal Growth Factor Receptor Tyrosine Kinase, *Science*, 1994, 265, 1093–1095.
J.M. Zgombick, Ketanserin and Ritanserin Discriminate Between Recombinant Human 5–HT$_{1D\alpha}$ and 5–HT$_{1D\beta}$ Receptor Subtypes, *Eur. J. Pharmacol Mol. Pharmacol. Sect.* 1995, 291, 9–15.

T. Kotani et al., Highly Selective Aldose Reductase Inhibitors. 3. Structural Diversity of 3–(Arylmethyl)–2,4, 4–trioxoimidazolidine–1acetic Acids, *J. Med. Chem.* 1997, 40, 684–694.
B.O. Buckman et al., Solid–Phase Synthesis of 1,3–Dialkyl Quinazoline–2,4–Diones, *Tetrahedron Lett.* 1996, 37, 4439–4442.
A. Smith et al., An Efficient Solid Phase Synthetic Route to 1,3–Disubstituted 2,4(1H,3H)–Quinazolinediones Suitable for Combinatorial Synthesis, *Bioorg. Med. Chem. Lett.* 1996, 6, 1483–1496.
S.H. DeWitt et al., "Diversomers": An Approach to Nonpeptide, Nonoligomeric Chemical Diversity, *Proc. Natl. Acad. Sci. USA* 1993, 90:6909–6913.
K.M. Short et al., The Synthesis of Hydantoin 4–Imides on Solid Support, *Tetrahedron Lett.* 1996 27, 7489–7492.
B.A. Dressman et al., Solid Phase Synthesis of Hydantoins Using a Carbamate Linker and a Novel Cyclization/Cleavage Step, *Tetrahedron Lett.*1996, 37, 937–940.
S. Hanessian et al., Solution and Solid Phase Synthesis of 5–Alkoxyhydantoin Libraries with a Three–Fold Functional Diversity, *Tetrahedron Lett.* 1996 37, 5835–5838.
J. Matthews et al., Base–Promoted Solid–Phase Synthesis of Substituted Hydantoins and Thiohydantoins, *J. Org. Chem.* 1997 62, 6090–6092.
Bayer Ernst (1991) "Towards the Chemical Synthesis of Proteins", *Angew. Chem. Int. Ed. Engl.*, 30: 113–129 (Exhibit 1).
Bicknell A. J., and Hird N. W., (1996) "Synthesis Of A Highly Functionalized Rigid Template By Solid Phase Azomethine Ylide Cycloaddition", *Bioorg. Med. Chem. Lett.*, 6: 2441–2443 (Exhibit 2).
Bonjouklian R., and Ruden R.A., (1977), "Versatile Allene and Carbon Dioxide Equivalents for the Diels–Alder Reaction", *J. Org. Chem.*, 42: 4095–4103 (Exhibit 3).
Chantegrel B., and Gelin S., (1981) "Synthesis of Some 1,2–Oxazoles bearing a Fused Heterocyclic Ring from $\alpha$–Acetylhomotetronic Acids", *Synthesis*, 4: 315–316 (Exhibit 4).
Diurno, et al., (1992) "Synthesis and Antihistaminic Activity of Some Thiazolidin–4–ones", *J. Med. Chem.*, 35: 2910–2912 (Exhibit 5).
Gordeev, et al., (1997) "A General and Efficient Solid Phase Synthesis of Quinazoline–2, 4–diones", *Tetrahedron Lett.*, 38(10): 1729–1732 (Exhibit 6).
Gouilleux, et al., (1996) "Solid Phase Synthesis of chiral 3–substituted Quinazoline–2, 4–diones", *Tetrahedron Lett.*, 37(39): 7031–7034 (Exhibit 7).

(List continued on next page.)

Primary Examiner—John M. Ford
(74) Attorney, Agent, or Firm—John P. White; Cooper & Dunham LLP

(57) ABSTRACT

Methods and compounds for the synthesis of heterocycles, including pyrimidine-2,4-diones, are disclosed. Also disclosed are solid supports useful for solid phase synthesis, and methods for making the solid supports.

4 Claims, 16 Drawing Sheets

OTHER PUBLICATIONS

Hamper, et al., (1996) "Solid–Phase Synthesis of Proline Analogs via a Three Component 1,3–Dipolar Cyloaddition", *Tetrahedron Lett.*, 37(21): 3671–3674 (Exhibit 8).

Hauke, et al., (1994) "Spiro–Triterpenes from Clay–Catalysed Rearrangement Elucidation and Occurrence in a a Recent Sediment", *Tetrahedron Lett.*, 35(14): 2227–2230 (Exhibit 9).

Hutchins S.M., and Chapman K. T., (1996) "Fischer Indole Synthesis on a Solid Support", *Tetrahedron Lett.*, 37(28): 4869–4872 (Exhibit 10).

Kiselyov A.S. and Armstrong R.W., (1997) "Solid Support Synthesis of Tetrahydroquinolines via the Grieco Three Component Condensation", *Tetrahedron Lett.*, 38(35): 6163–6166 (Exhibit 11).

Look, et al., (1996) "The Identification Of Cyclooxygenase–1 Inhibitors From 4–Thiazolidinone Combinatorial Libraries", *Bioorg. Med. Chem. Lett.*, 6(6): 707–712 (Exhibit 12).

MacDonald, et al., (1996) "A Solid Phase Approach to Quinolones using the Diversomer Technology", *Tetrahedron Lett.*, 37(27): 4815–4818 (Exhibit 13).

Marquais S., and Arlt M., (1996) "Aryl–Aryl Cross Coupling on a Solid Support using Zinc Organic Reagents and Palladium Catalysis", *Tetrahedron Lett.*, 37(31): 5491–5494 (Exhibit 14).

Moon, et al., (1994) "A Polymer–Supported $C_2$–Symmetric Chiral Auxiliary: Preparation Of Non–Racemic 3,5–Disubstituted–γ–Butyrolactones", *Tetrahedron Lett.*, 35(48): 8915–8918 (Exhibit 15).

Newkome G. R., and Nayak A., (1979) "4–Thiazolidinones", *Academic Press*, 25: 84–112 (Exhibit 16).

Ruhland, et al., (1996) "Solid–Supported Combinatorial Synthesis of Structurally Diverse β–Lactams", *J. Am. Chem. Soc.*, 118: 253–254 (Exhibit 17).

Singh, et al., (1981) "Chemistry and Biological Activity of Thiazolidinones", *Chem. Rev.*, 81: 175–203 (Exhibit 18).

Thompson L.A., and Ellman J. A., (1996) "Synthesis and Applications of Small Molecule Libraries", *Chem. Rev.*, 96: 555–600 (Exhibit 19).

Wang H., and Ganesan A., (1998) "Total Synthesis of the Quinazoline Alkaloids (–)–Fumiquinazoline G and (–)–Fiscalin B", *J. Org. Chem.*, 63: 2432–2433 (Exhibit 20).

FIGURE 4 Solid Phase Synthesis of Fused Bicyclic Thiazolidine Analogs

FIGURE 6

Examples of cyclocleavage reactions on solid phase

| R-NH₂ | Purity (%) | Yield (%) | R-NH₂ | Purity (%) | Yield (%) |
|---|---|---|---|---|---|
| piperonylamine (3,4-methylenedioxybenzylamine) | 98 | 76 | tryptamine | 98 | 80 |
| 3-(trifluoromethyl)benzylamine | 95 | 75 | 3-morpholinopropylamine | 96 | 77 |
| 3-methoxybenzylamine | 97 | 80 | 1-(3-aminopropyl)-2-pyrrolidinone | 93 | 72 |
| 3,4-dimethoxybenzylamine | 98 | 72 | 1-benzyl-3-aminopyrrolidine | 95 | 72 |
| 2-methoxybenzylamine | 93 | 73 | 3-phenylpropylamine | 91 | 80 |
| 2-(2,4-dichlorophenyl)ethylamine | 94 | 77 | 2-amino-4-phenylthiazole | 94 | 81 |

*Representative examples of analogs of phthalic anhydride*

FIGURE 14 Reaction Sequence in Solid Phase of Hydantoins

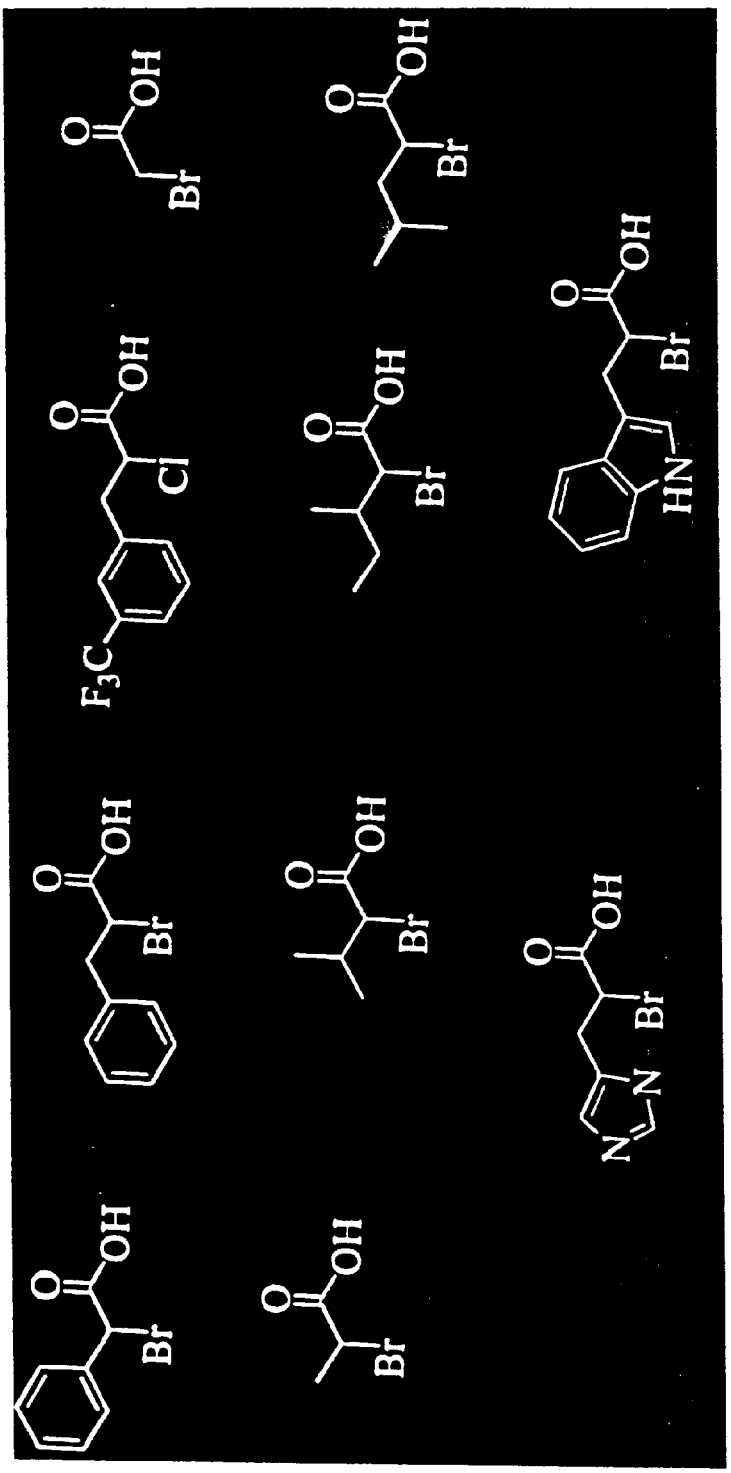
FIGURE 16 Building Blocks of Alpha-Halo Acids

SOLID PHASE SYNTHESIS OF HETEROCYCLES

RELATED APPLICATION

This application claims priority to U.S. Provisional Application Serial No. 60/066,878, filed Nov. 26, 1997, entitled "Solid Phase Synthesis of Heterocycles", the contents of which are hereby expressly incorporated by reference.

BACKGROUND OF THE INVENTION

In recent years solid phase organic synthesis has emerged as a powerful tool in high throughput synthesis to generate small molecular libraries for drug discovery process (for recent reviews on solid phase organic synthesis, see: (a) Balkenhohl, F.; von dem Bussche-Hunnefeld; Lansky, A.; Zechel, C. *Angew. Chem. Int. Ed. Engl.* 1996, 35, 2288. (b) Thompson, L. A.; Ellman, J. A. Chem. Rev. 1996, 96, 555. (c) Fruchtel, J. S.; Jung, G. *Angew. Chem. Int. Ed. Engl.* 1996 35, 17. (d) Hermkens, P. H. H.; Ottenheijm, H. C. J.; Rees, D. *Tetrahedron* 1996m 52, 4527. (e) Special issue, *Acc. Chem. Res.* 1996, 29). The chance of finding active lead compounds in a library depends on not only the molecular diversity, but also the key pharmacophoric heterocyclic templates. Examples of heterocyclic templates which have been reported include benzodiazepines ((a) Ellman, J. A.; Plunkett, M. J. *J. Am. Chem. Soc.* 1995, 117, 3306–3307), pyrrolidines ((b) Murphy, M. M.; Schullek, J. R.; Gordon, E. M.; Gallop, M. A. *J. Am. Chem. Soc.* 1995, 117, 7029–7030), beta-lactams ((c) Ruhland, B.; Bhandari, A.; Gordon, E. M.; Gallop, M. A. *J. Am. Chem. Soc.* 1995, 117, 253–254), and 4-thiazolidinediones ((d) Patek, M.; Drake, B.; Lebl, M. *Tetrahedron Lett.* 1995, 36, 2227–2230).

Another example of a heterocyclic template is the quinazoline-2,4-dione system. The quinazoline-2, 4-dione template appears in a wide range of bioactive molecules, including adrenergic, serotoncrgic, dopaminergic, endothelin $ET_A$ receptor ligands, and inhibitors of cyclooxygenase, collagenase, aldose reductase, and carbonic anhydrase (for recent examples, see: (a) Russo, *J Med. Chem.* 1991, 34, 1850. (b) Fry, D. W.; Kraker, A. J.; McMichael, A.; Ambroso, L. A.; Nelson, J. M.; Leopold, W. R.; Conners, R. W.; Bridges, A. J. *Science* 1994, 265, 1093–1095. (c) Zgombick, 1995, *Eur. J Pharmacol. Mol. Pharmacol. Sect.* 1995, 291, 9. (d) Kotani, T.; Nagaki, Y.; Ishii, A.; Konishi, Y. *J Med. Chem.* 1997, 40, 684–694).

Classical techniques of organic synthesis have generally entailed the use of solution-phase reactions for the preparation of organic compounds of interest. However, purification of organic molecules after solution-phase synthesis can be a tedious and sometimes expensive process, which can result in slow throughput and decreased yields of desired compounds. The poor solubility of certain heterocyclic compounds can additionally complicate synthesis of these compounds. Solid-phase synthesis (SPS) on a solid or insoluble support is an approach which can obviate some purification-related problems of solutions-phase synthesis is synthesis.

For example, there have been several recent reports of solid phase synthesis of quinazoline-2, 4-diones. One of the first methods was described by Buckman and Mohan, using a special linker prepared by multiple step synthesis and the phthalic half-ester to generate the bicyclic structure (Buckman, B. O.; Mohan, R. *Tetrahedron Lett.* 1996, 37, 4439–4442). Another method, reported by Smith and Gouilleux separately, involved the thermal cyclization through urethane protected anthranilamide (Smith, A.; Thomson, C. G.; Leeson, P. D. *Bioorg. Med. Chem. Lett.* 1996, 6, 1483; Gouilleux, L.; Fehrentz, J. A.; Winternitz, F.; Martinez, J. *Tetrahedron Lett.* 1996, 37, 7031–7034). Another reported method uses tetramethylguanidine with amino acids as the linkers on the solid support (Gordeev, M. F.; Hui, H. C.; Gordon, E. M.; Patel, D. V. *Tetrahedron Lett.* 1997, 38, 1729–1732). All of these methods use anthranilic acids as the starting materials. However, some of these reported methods involve the use of harsh conditions (such as the use of strong bases or high temperatures), do not provide uniformly high yields, or are not generally applicable to synthesis of a wide variety of quinazoline-2,4-diones.

Hydantoins represent the basic structure of a number of CNS agents, especially in antiepileptics area, of which phenytoin is an example which is still on the market. Recently, Fosphenytoin, a hydantoin introduced by Parke-Davis, was approved by FDA as the prodrug of phenytoin. Recently, several groups have reported the synthesis of hydantoins on solid phase. DeWitt and her colleagues at Parke-Davis described the synthesis of 40 hydantoins (*Proc. Natl. Acad. Sci. USA* (1993), 90:6909–6913; and WO 94/08711, 1994). Other references to synthesis of hydantoins include Short, K. M. et al., *Tetrahedron Lett.* (1996) 37, 7489–7492; Dressman, B. A. et al., *Tetrahedron Lett.* (1996) 37, 937–940; Hanessian, S. et al. *Tetrahedron Lett*, (1996) 37, 5835–5838; and Mattews, J. et al., *J. Org. Chem* (1997) 62, 6090–6092. However, improved methods for synthesis of hydantoins are needed.

SUMMARY OF THE INVENTION

In one aspect, the invention provides a method for preparing a substituted or unsubstituted pyrimidine-2,4-dione, e.g., a compound having the structure:

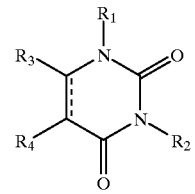

in which the dashed line represents an optional bond; $R_1$ and $R_2$ are each, independently, hydrogen, alkyl, or aryl; $R_3$ and $R_4$ are each, independently, hydrogen, halogen, alkyl, or aryl; or $R_3$ and $R_4$ are joined to form a ring having from 5 to 7 atoms in the ring moiety.

In another aspect, the invention provide a method for preparing a compound on a solid support.

In yet another aspect, the invention provides a method for preparing a solid support suitable for use in solid phase synthesis. The method includes the steps of preparing the sodium alkoxide of short-chain linear polyethylene glycol by reacting the short-chain linear polyethylene glycol with sodium hydride; and reacting the sodium alkoxide of short-chain linear polyethylene glycol with chloromethylpolystyrene, such that a graft copolymer is prepared.

These and other objects, features, and advantages of the invention will be apparent from the following description and claims.

BRIEF DESCRIPTION OF THE DRAWINGS

FIG. 6 is a table showing reaction yields and purities for exemplary syntheses according to methods of the invention.

FIG. 16 shows building blocks of alpha-halo acids useful in the preparation of hydantoins.

DETAILED DESCRIPTION OF THE INVENTION

I. Methods for Preparing Pyrimidine-2,4-diones

Figure 1:
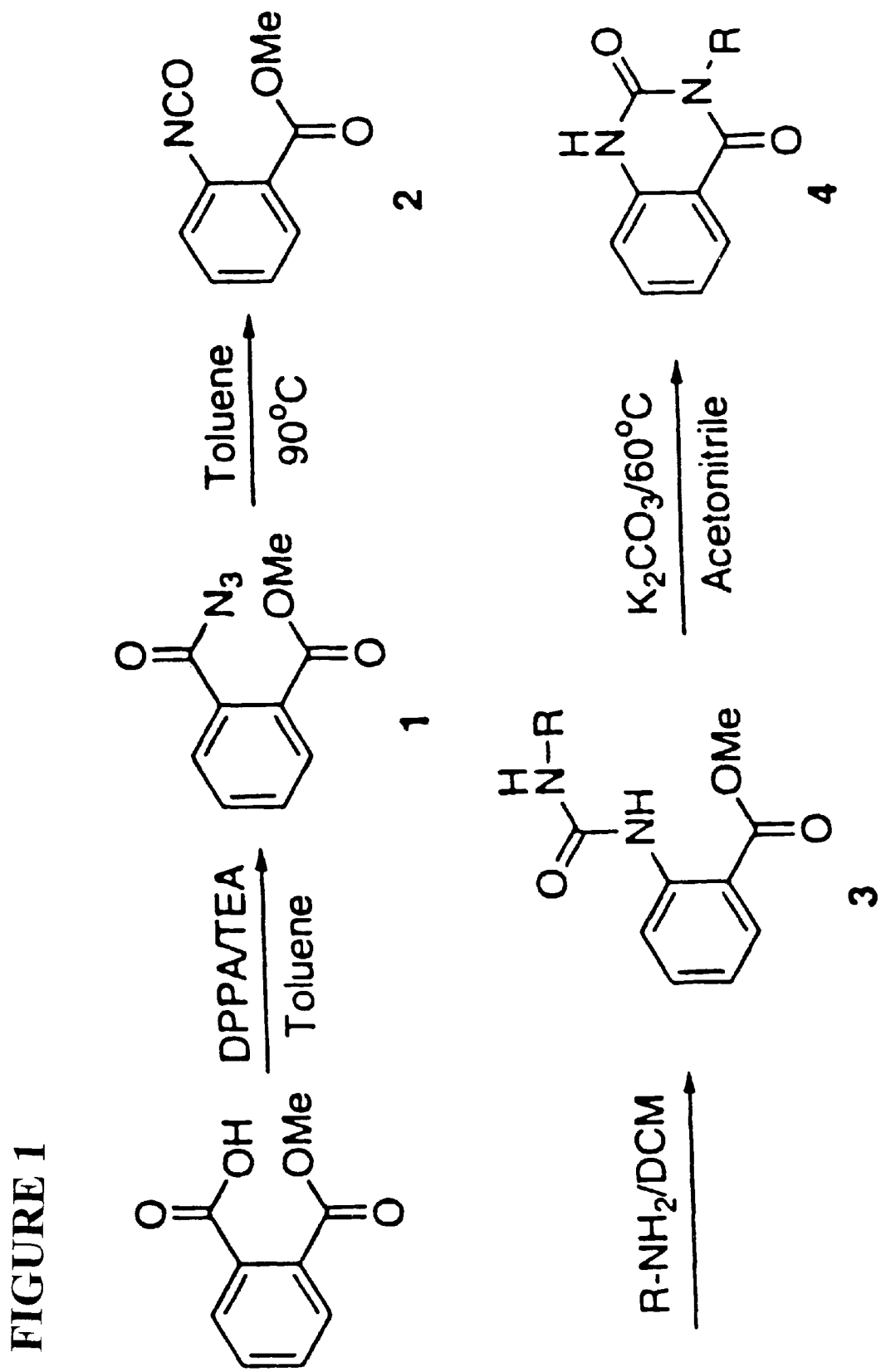
FIG. 1 schematically depicts a solution-phase synthesis of quinazoline-2,4-diones.

In one aspect, the invention provides concise and practical methods for preparing structurally diverse small molecule libraries (e.g., of pyrimidine-2,4-diones) on solid phase. In the inventive methods, only the desired product(s) is generated and released from the solid support. A simultaneous cyclization/cleavage reaction on the solid support occurs as the final synthetic step, preferably under mild conditions, to release the desired compound(s).

In one embodiment, the invention provides a method for preparing a substituted or unsubstituted pyrimidine-2,4-dione, e.g., compound represented by the formula (Formula I):

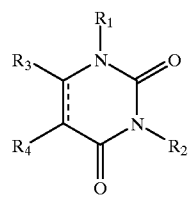

in which the dashed line represents an optional bond; $R_1$ and $R_2$ are each, independently, hydrogen, alkyl, or aryl; and $R_3$ and $R_4$ are each, independently, hydrogen, halogen, alkyl, or aryl; or $R_3$ and $R_4$ are joined to form a ring having from 5 to 7 atoms in the ring moiety. The method includes the step of reacting a compound represented by the formula (Formula II):

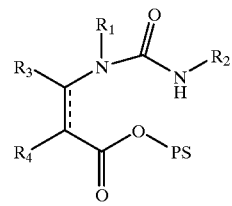

in which $R_1$, $R_2$, $R_3$, and $R_4$ are as described above, and PS is a polymer support, under conditions such that the compound of Formula I is prepared. In certain preferred embodiments, the step of reacting the compound of Formula I under conditions such that the compound of Formula I is formed comprises contacting the compound of Formula II with an effective ring-closing amount of $M_nCO_3$, in which M is an alkali metal or an alkaline earth metal (preferably potassium), and n is 1 or 2. In certain embodiments, the compound of Formula I is a quinazoline-2,4-dione, e.g., the compound of Formula I is represented by the formula (Formula III):

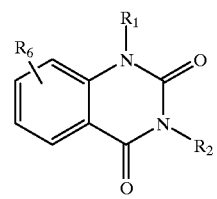

in which $R_6$ represents zero to four substituents each independently selected from the group consisting of halogen, hydroxy, alkoxy, alkyl, aryl, mercapto, and alkylthio. It will be appreciated that in embodiments, in which $R_3$ and $R_4$ are joined to form a ring, the ring can substituted or unsubstituted, and can be carbocyclic (e.,g., a cyclohexane ring or a benzene ring) or heterocyclic (e.g., a piperidine, piperazine, pyrrole, pyridine, furan, or thiophene ring). In a preferred embodiment, the polymer support (PS) can be represented by the formula —$(CH_2CH_2O)_m$-polymer, in which m is an integer between 3 and 5, and polymer is a methylbenzene-divinylbenzene copolymer.

Examples of pharmaceutically important quinazoline-2,4-diones which can be synthesized by the methods of the present invention include, for example:

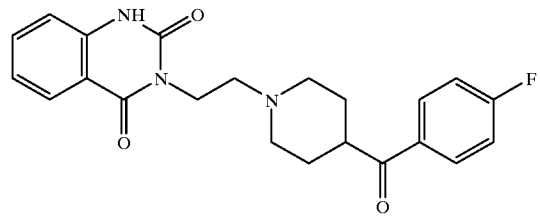

which is a selective 5-HT receptor antagonist (*Life Science* 28:1015 (198 1)),

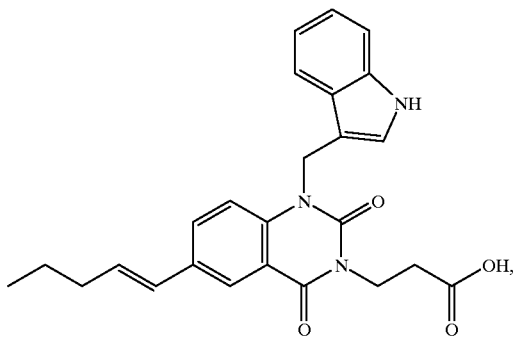

a specific endothelin ET$_A$ receptor antagonist (WO 9515963),

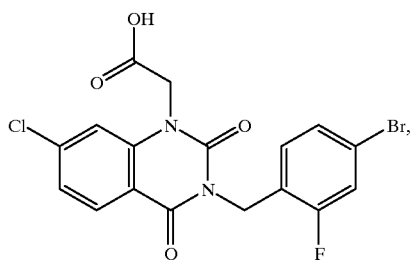

FK366, an aldose reductase inhibitor (ARI) (*J. Med. Chem.* 40:684 (1997)) and

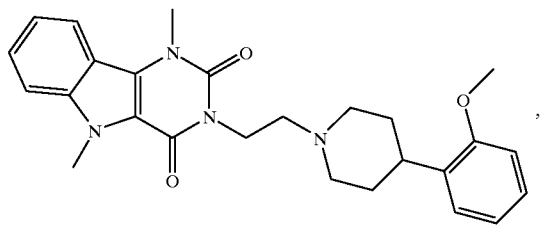

a selective alpha-1 adrenoceptor ligand (*J. Med. Chem.* 34:1850 (1991)).

The compound of Formula II can be prepared according to a variety of methods, some of which are described herein (see, e.g., Examples 1, 3, and 4, infra), and others which will be apparent to one of ordinary skill in the art. For example, a compound of Formula II can be prepared by immobilizing a diacid, or a suitable derivative of a diacid, such as phthalic acid, succinic acid, or maleic acid (e.g., as the anhydride), on a suitable polymer support (PS), such as a hydroxyl-functionalized support, e.g., Tentagel, or a graft copolymer prepared by reaction of short-chain PEG-with chloromethylpolystyrene as described herein. A coupling reagent can be employed to facilitate immobilization of the diacid (or derivative thereof) on the solid support, if desired. However, in a preferred embodiment, the diacid is provided as the anhydride, which will generally be sufficiently activated to react with the solid support without use of additional coupling reagents, although a base such as pyridine, triethylamine, or diisopropylethylamine, can be employed, optionally in combination with a catalyst such as 4-dimethylaminopyridine (DMAP).

The immobilized diacid (e.g., a compound of Formula IV, see infra) can then be converted to the corresponding immobilized acyl azide, e.g., with diphenylphosphoryl azide (DPPA), as described in Example 3, infra, followed by Curtius rearrangement to the corresponding isocyanate. The isocyanate can then be converted to a compound of Formula II by treatment with an amine, e.g., as described herein.

An alternate synthesis of a compound of Formula II begins with a substituted or unsubstituted β-amino acid (including 1,2-substituted aromatic amino acids, such as anthranilic acid), e.g., in which the amino group is protected, e.g., as the t-butoxycarbonyl (Boc) derivative. The N-protected β-amino acid is immobilized on a polymer support, e.g., with use of a coupling reagent or by conversion to the acid chloride. The immobilized protected β-amino acid is deblocked by treatment with trifluoroacetic acid (TFA), and the amino group is then converted to the urea, e.g., by treatment with an isocyanate.

It will be apparent to the ordinarily skilled artisan that compounds related to compounds of Formula II (e.g., urea derivatives), but having a free carboxylate group (i.e., not immobilized on the solid support) can be prepared in solution, followed by immobilization on the polymer support.

Once the compound of Formula II has been prepared (i.e., suitably functionalized and immobilized on the solid support), the compound of Formula II is subjected to reaction conditions suitable for allowing ring closure to provide a compound of Formula I. For example, in the synthesis depicted in FIG. 1, a key step was to find suitable conditions to close the ring and generate the bicyclic structure 4. In previous publications, high temperature (125° C. in DMF; Buckman, B. O.; Mohan, R. *Tetrahedron Lett.* 1996, 37, 4439–4442), and/or strong basic conditions (KOH in ethanol (Smith, A.; Thomson, C. G.; Leeson, P. D. *Bioorg. Med. Chem. Lett.* 1996, 6, 1483) or tetramethylguanidine at 60° C. (Gordeev, M. F.; Hui, H. C.; Gordon, E. M.; Patel, D. V. *Tetrahedron Lett.* 1997, 38, 1729–1732))) were reported. However, milder conditions, more compatible with synthesis of a wide variety of functional groups, are desirable. It has now been found that treatment of a compound of Formula II with solid (preferably finely divided or powdered) potassium carbonate (or another metal carbonate such as lithium, sodium, barium, cesium, and the like) can smoothly promote ring closure under relatively mild conditions, e.g., to convert compounds of Formula II to compounds of Formula I in high yield and purity (see, e.g., Example 3–4). Thus, in a preferred embodiment of the methods of the invention, a compound of Formula I is contacted with an amount of solid potassium carbonate sufficient to promote ring closure and cleavage of the resultant pyrimidine-2,4-dione product from the solid support, such that the compound of Formula I is prepared. The effective amount of the carbonate base will generally be at least one equivalent per equivalent of the immobilized compound of Formula II. In certain embodiments, at least 1.5 equivalents, 2 equivalents, 5 equivalents, or 10 equivalents of the carbonate base are employed to effect ring closure and cleavage of the product from the solid support.

The use of a base such as potassium carbonate avoids use of strong bases, and high temperatures are generally not required for the ring-closing reaction to proceed in a reasonable time. Additionally, use of a solid inorganic base permits removal of the base from the reaction mixture by simply filtration, thereby reducing the need for additional purification steps to remove the base. Thus, the desired cyclized compounds, released from the polymer support by the cyclization/cleavage reaction, can be isolated in high purity by simply removing the reaction solvent, e.g., by distillation or removal in vacuo. It has further been found that use of a solid inorganic base, such as a metal carbonate, e.g., potassium carbonate, is useful for promoting other cyclization/cleavage reactions. For example, as described in Example 5, infra, use of potassium carbonate also promotes the cyclization and cleavage of hydantoins from a solid support of the invention. Thus, in another aspect, the invention relates to the use of a solid inorganic base, such as a metal carbonate, e.g., potassium carbonate, to promote cyclization or cleavage reactions of an immobilized compound, e.g., to promote formation of a heterocyclic compound. The reaction(s) is preferably performed in a polar aprotic solvent, such as, e.g., dimethylacetamide.

In another embodiment, the invention provides a method for preparing a compound represented by the formula (Formula IV):

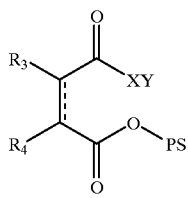

in which the dashed line represents an optional bond; $R_3$ and $R_4$ are each, independently, hydrogen, halogen, alkyl, or aryl; or $R_3$ and $R_4$ are joined to form a ring having from 5 to 7 atoms in the ring moiety; X is O or S; Y is H or a salt-forming cation; and PS is a polymer support. The method includes the step of reacting a compound represented by the formula (Formula V):

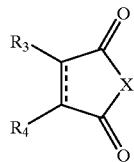

in which $R_3$ and $R_4$ are as described above, and X is O or S, with a polymer support having free hydroxyl groups under conditions such that a compound of Formula IV is formed. In a preferred embodiment, X is O (i.e., the compound of Formula V is an anhydride). Thus, in a preferred embodiment, the invention features the reaction of an anhydride of Formula V, in which X is oxygen, with a polymer support having free hydroxyl groups, such that a compound of Formula IV (in which X is O) is formed. It will be appreciated that Y can be H, or, if the reaction is carried out in the presence of a base, can be any salt-forming cation, including, e.g., lithium, sodium, potassium, calcium, magnesium, barium, aluminum, ammonium, alkylammonium, and the like.

In general, the reactions according to the invention will be performed in a liquid medium, e.g., in a suspension of a solid support in a liquid medium. It will be appreciated that preferred reaction solvents include solvents in which the carbonate base, such as potassium carbonate, is not substantially soluble. The reactions are preferably run in an inert solvent, and, in certain embodiments, the solvent is capable of swelling the polymer support. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide, dimethylacetamide (DMA) and the like; or combinations of two or more solvents. The reactions can be conducted under anhydrous conditions, although in certain embodiments, protic solvents, including, e.g., water, methanol, ethanol, isopropanol, and the like, can be employed. In certain embodiments it is preferable to perform the reactions under an inert atmosphere of a gas such as nitrogen or argon.

The progress of the reactions can be monitored by techniques known to one of ordinary skill in the art. For example, aliquots of the reaction mixture can be taken at intervals and the aliquots tested, e.g., by cleavage of compounds from the solid support followed by spectroscopic analysis of the crude reaction mixture. Alternatively, the reaction can be monitored by chromatographic techniques such as thin-layer chromatography (TLC) or HPLC.

In certain embodiments, the methods for preparing compounds include the further step of purifying the compounds. Purity of the reaction products can be determined according to known techniques. If the products are impure, they can be purified according to a variety of methods known in the art. For example, compounds immobilized on a solid support can be separated from some impurities by simple filtration and washing of the solid support to remove soluble impurities. Compounds which are not immobilized on solid supports can be purified by methods including crystallization (where the compound is crystalline), trituration, distillation, and chromatographic techniques such as TLC and HPLC (analytical or preparative scale), flash chromatography, and the like. The selection of methods for purifying compounds will be routine for the ordinarily skilled artisan.

In preferred embodiments, the purity of a compound produced according to the methods of the invention is at least about 50%, more preferably at least about 70%, still more preferably at least about 90%, and most preferably at least about 95%.

The invention also relates to solid supports suitable for solid-phase synthesis of organic compounds, and to methods for making and using the solid supports. In one aspect, the invention provides a method for preparing a polymeric solid support suitable for use in solid phase synthesis. The method includes the steps of preparing the sodium alkoxide of short-chain linear polyethylene glycol by reacting the short-chain linear polyethylene glycol with sodium hydride; and reacting the sodium alkoxide of short-chain linear polyethylene glycol with chloromethylpolystyrene, such that a solid support having hydroxyl groups, e.g., of immobilized short-chain linear polyethylene glycol, is prepared. In a preferred embodiment, the step of reacting the sodium alkoxide of short-chain linear polyethylene glycol with chloromethylpolystyrene is performed in an aprotic solvent, more preferably a polar aprotic solvent such as dimethylformamide, dimethylsulfoxide, or, most preferably, dimethylacetamide (see, e.g., Example 2).

It has been reported that graft copolymers of polyethylene glycol (PEG)-polystyrene (PS) can provide hydrophilic reaction environment on solid support (Bayer, E. *Angew. Chem. Int. Ed. Engl.* 1991, 30, 113–216). However, use of long-chain polyethylene glycol to prepare a solid support has certain disadvantages: both of the hydroxyl terminals of the long PEG chains (>800 Da) can react with (for example)

chloromethylated PS and lead to low loading capacity on polymer; in addition, long PEG chains tend to break down in organic reaction and contaminate the product. It is believed that many of these disadvantages can be avoided by preparation of a solid support according to the methods of the invention. According to the invention, a solid support suitable for solid-phase synthesis of organic compounds is provided by use of short-chain and linear polyethylene glycol (~200 Da, approximately 4 units of ethylene glycol) to prepare the support. As described in Example 2, infra, good loadings of short-chain linear polyethylene glycol on the polymer matrix were obtained by reaction of short-chain PEG with sodium hydride, followed by reaction with Merrifield resin in DMA for about 24 hours at 0° C. This reaction time compares favorably to a reported synthesis of solid supports, in which a PEG was reacted with a solid support for 120 hours (see U.S. Pat. No. 4,908,405 to Bayer and Rapp). Thus, in preferred embodiments, the reaction with the chloromethylpolystyrene is performed for a time period not longer than about 72 hours, more preferably not more than about 48 hours, and still more preferably not more than about 24 hours. Moreover, the methods of the invention afford a support with good loadings of hydroxy groups, e.g., in preferred embodiments, a solid support of the invention has at least 1.0, more preferably at least about 1.2, 1.4, 1.6, 1.8 or 2.0 meq of hydroxyl groups per gram of resin. Thus, the invention also relates to a solid support comprising a functionalized polystyrene (or copolymer of polystyrene such as polystryene/divinylbenzene copolymer) having short-chain (e.g., in the range of about 3 to about 5, more preferably 4) linear polyethylglycol chains covalently bound thereto. Preferably, the solid support has about at least 1.0, more preferably at least about 1.2, 1.4, 1.6, 1.8 or 2.0 meq of hydroxyl groups per gram of resin, e.g., free hydroxyl groups available for reaction with a compound to be immobilized on the solid support.

In yet another aspect, the invention provides a method for synthesizing organic compounds by solid-phase synthesis on a solid support. In one embodiment, the method includes the steps of immobilizing a precursor compound (i.e., a compound to be modified in a subsequent solid-phase reaction) on a solid support, and reacting the precursor compound on the solid support under conditions such that an organic compound is prepared. The solid support is a graft copolymer of short-chain polyethylene glycol (e.g., from 3 to 5 ethylene glycol units) on a polymer backbone. In a preferred embodiment, the solid support is a polymer support (PS) that can be represented by the formula —(CH$_2$CH$_2$O)$_m$-polymer, in which m is an integer between 3 and 5, and polymer is a functionalized polystyrene/ benzene-divinylbenzene copolymer. The polymer support can be prepared by reaction of the sodium alkoxide of short-chain PEG (e.g., prepared by reaction of short-chain PEG with sodium hydride) with chloromethylpolystyrene, e.g., as described herein.

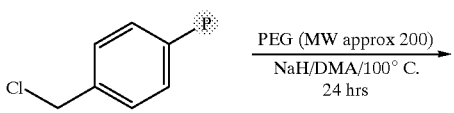

PEG (MW approx 200)
NaH/DMA/100° C.
24 hrs

-continued

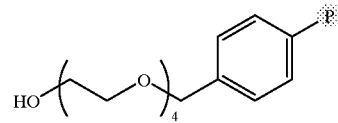

Common Tental-Gel Resins are less robust than Merrifield type resins, having 3000–4000 MW PEG with considerable contamination of PEG in the product, a low loading capacity (0.2–0.3 mmol/g) and a high cost for automated synthesis. In contrast, short-chain PEG Resins, as depicted above, are robust (200 M.W. PEG), have minimal if any contamination, having high loading capacities (1.5 mmol/g), which are easily prepared in the laboratory on 100 gram scale and produce about 10 mg of product (400 MW) from about 100 mg of resin.

It will be appreciated that the solid support preferably is not a graft copolymer of long PEG chains on the short-chain PEG resin, e.g., the resin is not a hydroxyl-functionalized resin such as those commercially available under the tradename Tentagel. In certain embodiments, the method includes the further step of purifying the organic compound. In certain embodiments, the nucleophile is provided as a variegated population of nucleophiles, such that a library of organic compounds is prepared.

The solid support of the invention is useful for preparing organic compounds by solid phase synthesis under conditions well known to one of ordinary skill in the art. For example, the solid supports of the invention can be used in place of conventional solid supports such as Wang resin, Rapp resin, and other hydroxyl-functionalized solid supports. As exemplified by the Examples herein, the solid support is useful for preparing compounds wherein the compounds are released from the support by a cyclocleavage reaction. Thus, the invention provides methods for the synthesis of, e.g., pyrimidine-2,4-diones, hydantoins, benzodiazepines, diketopiperazines, and the like. The solid supports of the invention are also useful for syntheses which involve reactions such as aromatic substitution (see, e.g., A. A. MacDonald et al., (1996) Tetrahedron Lett. 37:4815); Pd-catalyzed cross-couplings such as the Suzuki reaction (see, e.g., S. Marquois and M. Arlt (1996) Tetrahedron Lett. 37:5491); Fischer indole synthesis (see, e.g., S. M. Hutchins and K. T. Chapman (1996) Tetrahedron Lett. 37:4869)), synthesis of thiazolidines (see, e.g., M. Patek et al., (1995) Tetrahedron Lett. 36:2227; iodolactonization (see, e.g., H. S. Moon et al. (1994) Tetrahedron Lett. 35:8915); and the like.

Figure 2:
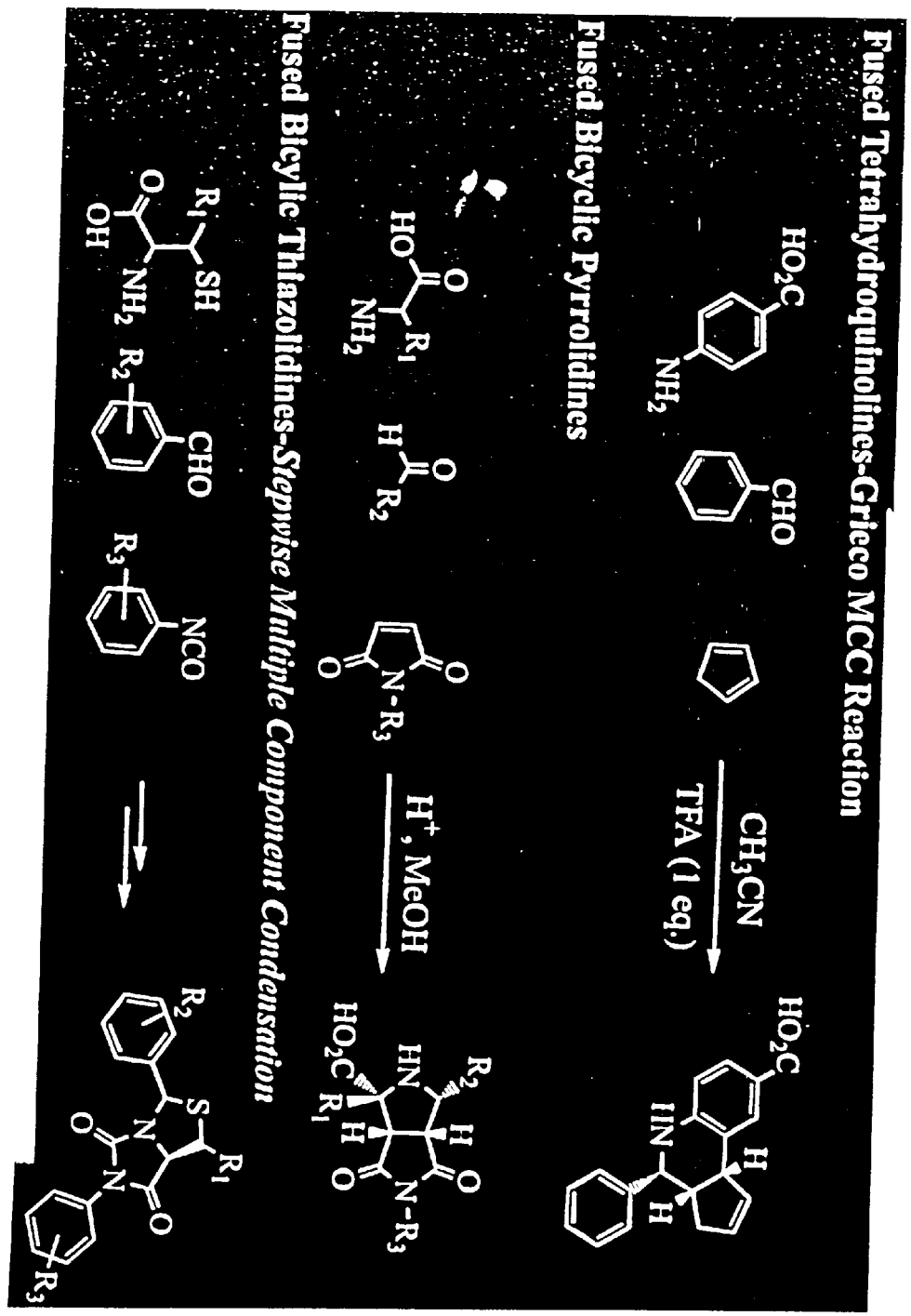
FIG. 2 shows traditional syntheses of thiazolidine analogs.

Prior to the present invention, thiazolidine analogs have been prepared by various methods including condensation of an amino-carboxylic acid and an aldehyde with a diene (Grieco MCC Reaction), condensation of an amino-carboxylic acid and an aldehyde with an activated olefin and by reaction of an amino-carboxylic acid, an aldehyde and an isocyanate as depicted in FIG. 2 (see, e.g., Amstrong, R. W. et al., Tetrahedron Lett. 38:6163 (1997); Hird, N. W. et al., Bioorg. Med. Chem. Lett. 6:2441 (1996); South, M. S. et al., Tetrahedron Lett. 37:3671 (1996). Biologically significant thiazolidine-based molecules which can be prepared by the methods of this invention include, for example

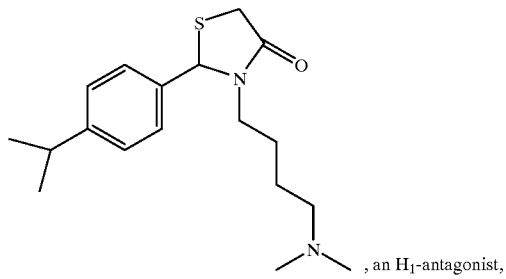, an H₁-antagonist,

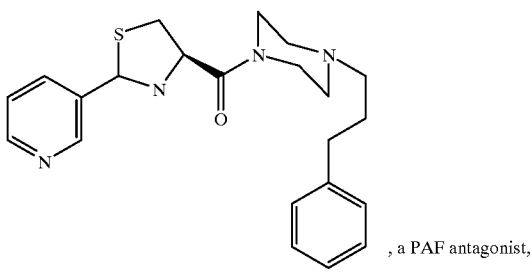, a PAF antagonist,

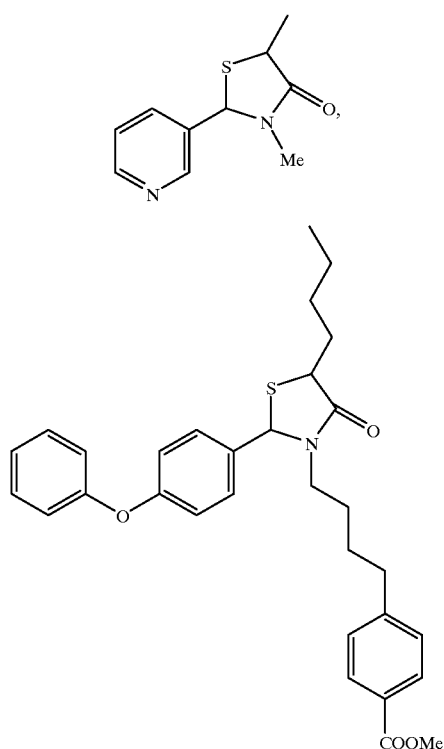

and (See, e.g., Diurno, M. V. et al., *J Med. Chem Lett.* 35:2910 (1992); Yamada, *Trends in Pharm. Sci.* 10:256 (1989); Look, G. C. et al., *Bioorg. Med. Chem. Lett.* 6:707 (1996); Singh, S. P. et al., *Chem. Rev.* 81:175 (1981); and Newkome, G. R. et al., *Advances in Hetero. Chem.* 25: 83 (1979).

The method of the invention includes treating a PEG supported protected amino acid with an aldehyde and an isocyanate followed by cleavage under mild conditions with base, $M_nCO_3$, e.g., $K_2CO_3$, as depicted below.

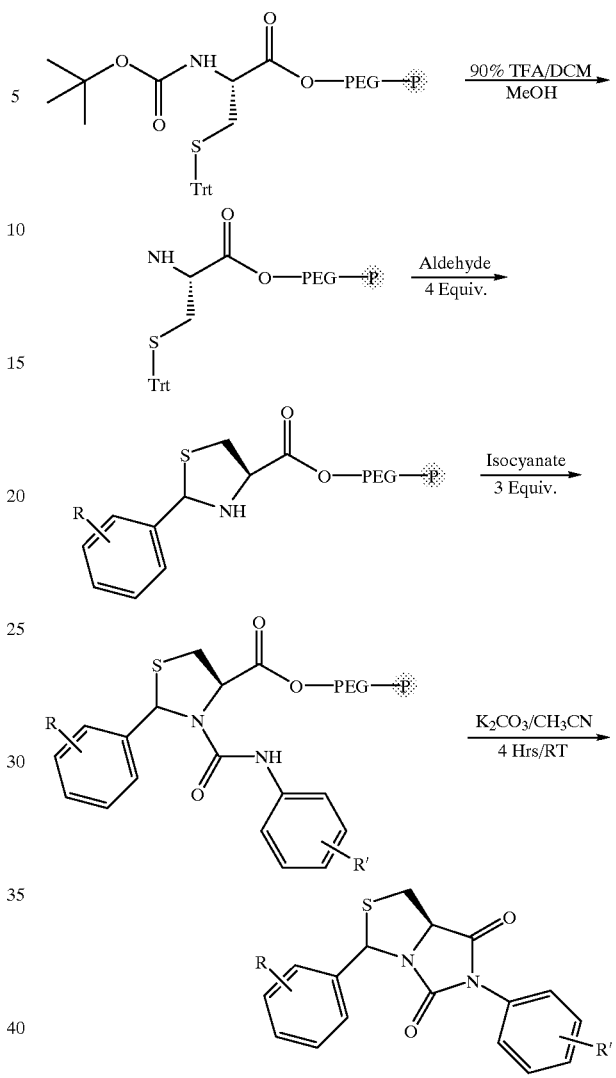

Figure 3:
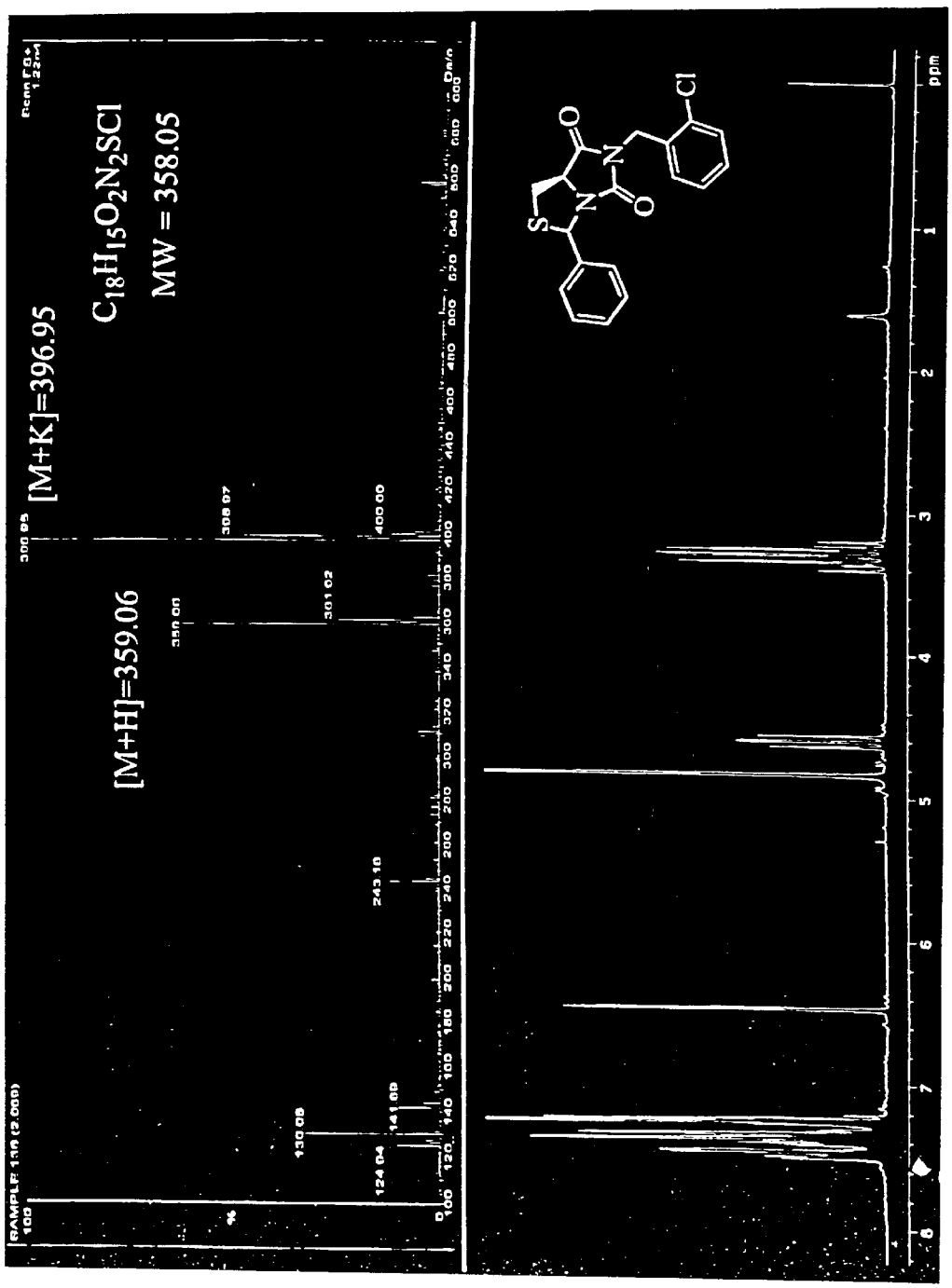
FIG. 3 depicts $^1$H NMR and MS results of a fused bicyclic thiazolidine analog produced by the method of the invention.
Figure 4:
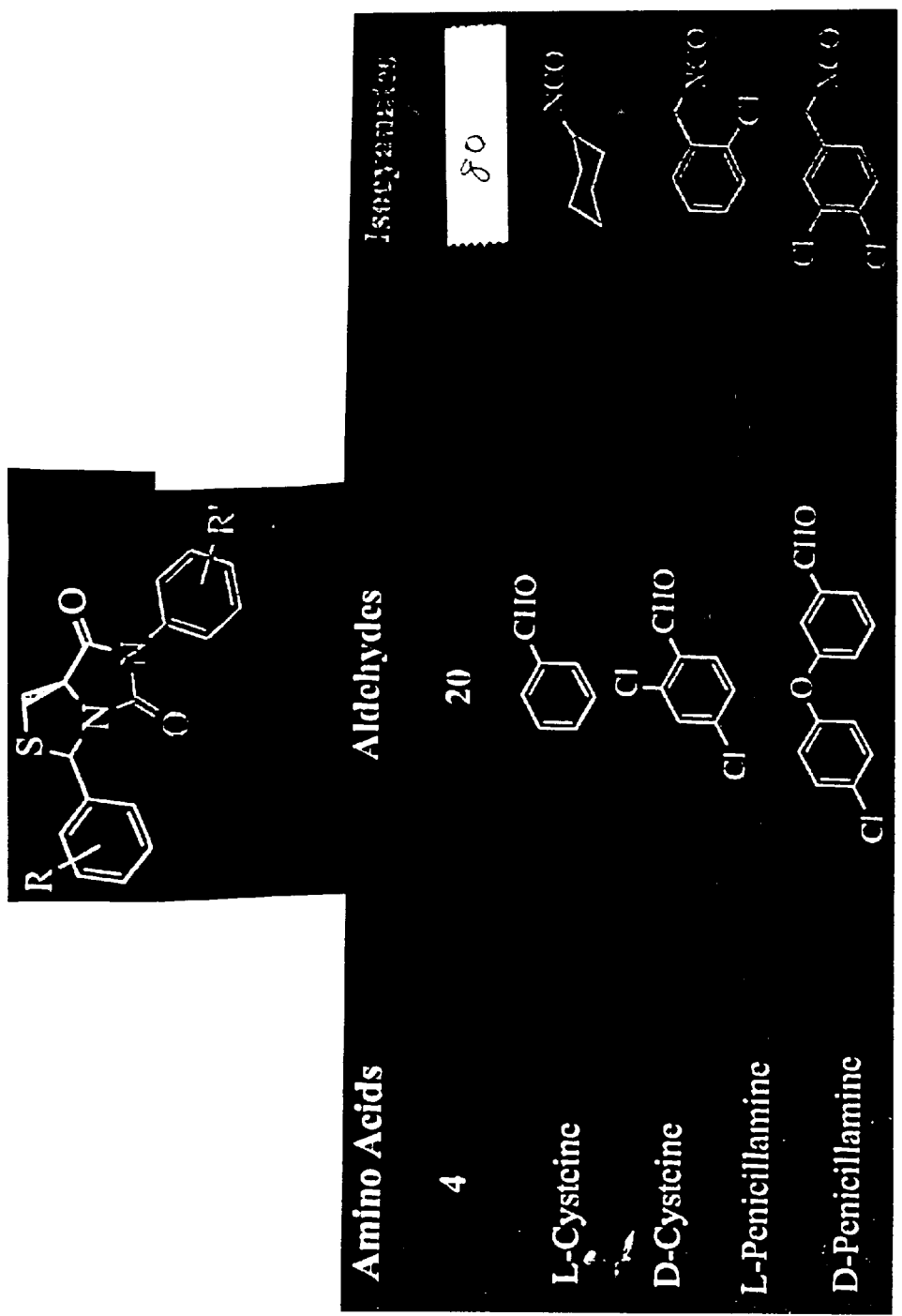
FIG. 4 depicts solids phase synthesis of fused bicyclic thiazolidine analogs prepared by the methods of the invention.

FIGS. 3 and 4 depict $^1$H NMR and MS of new fused bicyclic thiazolidine analogs and related combinations of amino acids, aldehydes and isocyanates used to Generate a library of thiazolidine analogs.

II. Compounds

In another aspect, the invention relates to compounds, e.g., compounds of Formulas I–V. The compounds of the invention can be prepared, e.g., by the methods described herein, or by methods known to the ordinarily-skilled artisan.

In one embodiment, the invention provides a compound represented by the formula (Formula II):

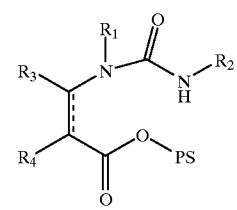

in which the dashed line represents an optional bond; $R_1$ and R2 are each, independently, hydrogen, alkyl, or aryl, $R_3$ and $R_4$ are each. independently, hydrogen, halogen, alkyl, or aryl; or $R_3$ and $R_4$ are joined to form a ring having from 5 to 7 atoms in the ring moiety. In a preferred embodiment, $R_3$ and $R_4$ are joined to form an aromatic ring, e.g., the compound of Formula II can be represented by the formula (Formula III):

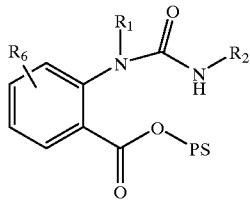

in which $R_1$ and $R_2$ are as described above, and $R_6$ represents zero to four substituents each independently selected from the group consisting of halogen, hydroxy, alkoxy, alkyl, aryl, mercapto, and alkylthio. It will be appreciated that in embodiments, in which $R_3$ and $R_4$ are joined to form a ring, the ring can substituted or unsubstituted, and can be carbocyclic (e.g., a cyclohexane ring or a benzene ring) or heterocyclic (e.g., a piperidine, piperazine, pyrrole, pyridine, furan, or thiophene ring). In a preferred embodiment, the polymer support (PS) can be represented by the formula —$(CH_2CH_2O)_m$-polymer, in which m is an integer between 3 and 5, and polymer is a methylbenzene-divinylbenzene copolymer.

In another embodiment, the invention provides a compound represented by the formula (Formula IV):

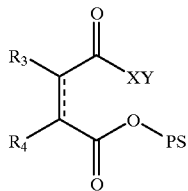

in which the dashed line represents an optional bond; $R_3$ and $R_4$ are each, independently, hydrogen, halogen, alkyl, or aryl; or $R_3$ and $R_4$ are joined to form a ring having from 5 to 7 atoms in the ring moiety; X is O or S; Y is H or a salt-forming cation; and PS is a polymer support. In preferred embodiments, X is O. In a preferred embodiment, the polymer support (PS) can be represented by the formula —$(CH_2CH_2O)_m$-polymer, in which m is an integer between 3 and 5, and polymer is a methylbenzene-divinylbenzene copolymer.

In still another aspect, the invention provides a compound represented by the formula (Formula VI):

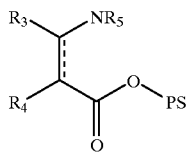

in which the dashed line represents an optional bond; $R_3$ and $R_4$ are each, independently, hydrogen, halogen, alkyl, or aryl; or $R_3$ and $R_4$ are joined to form a ring having from 5 to 7 atoms in the ring moiety; $NR_5$ is NCX or NHC(X)-LG, in which LG is a leaving group selected from the group consisting of alkoxy and halogen; X is O or S; and PS is a polymer support. In a preferred embodiment, $NR_5$ is NCX, in which X is O.

The invention also provides quinazoline-2,4-diones, hydantoins, and other compounds prepared according to the methods of the present invention.

Exemplification

All reagents were obtained from commercial suppliers and were used as received unless otherwise stated.

EXAMPLE 1

To develop suitable reaction conditions for solid phase synthesis, we initially investigated the synthesis in solution (FIG. 1 ) Starting with phthalic monomethyl ester, the acid group was converted to the acyl azide 1 with diphenylphosphoryl azide (DPPA), followed by Curtius rearrangement to afford the corresponding isocyanate 2 very cleanly ((a) Bonjouklian, R.; Ruden, R. A. *J Org. Chem.* 1977, 42, 2095. (b) Chantegrel, B.; Gelin, R. A. *Synthesis* 1981, 315). The isocyanate was transformed to urea 3 in the presence of primary amine and then the cyclization occurred under basic conditions to form the quinazoline-2, 4-dione structure 4. We found that $K_2CO_3$ in organic solvent (toluene, DMF, or acetonitrile) at 60° C. efficiently yields the desired product 4. In addition, $K_2CO_3$ can be easily removed by filtration after cyclization of the compound on the solid support has occurred.

EXAMPLE 2

Figure 5:
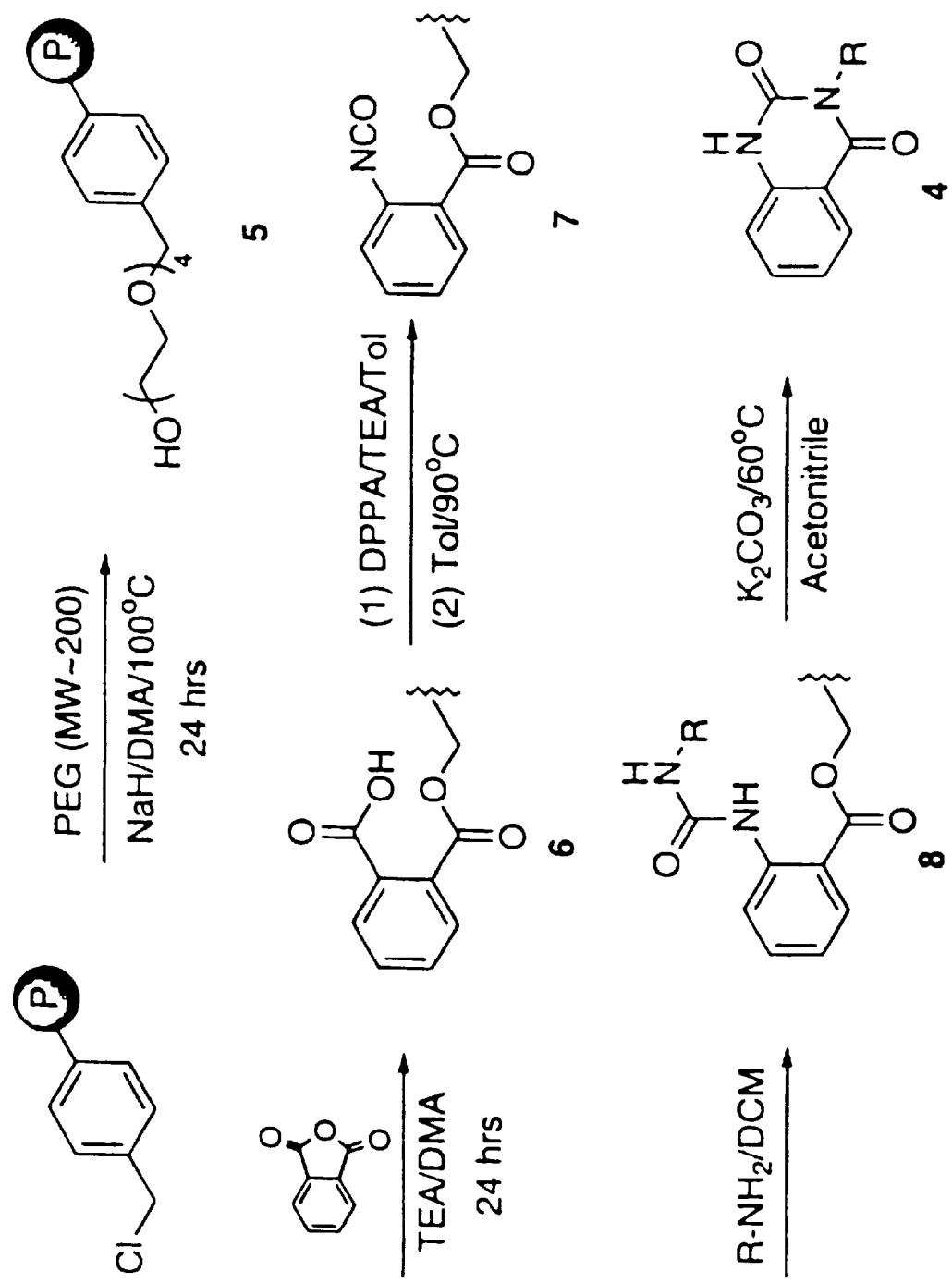
FIG. 5 shows a solid-phase synthesis of quinazoline-2,4-diones.

After appropriate cyclization conditions in solution were established (Example 1, supra), we developed a suitable linker for cyclization on solid phase using an automated synthesizer (Advanced ChemTech (ACT) model 496). As shown in FIG. 5, the short-chain PEG linker was easily introduced on Merrifield resin using the sodium alkoxide of PEG (10 equiv.). The graft copolymer of short-chain PEG-PS was made in 75 gram scale: To a stirred solution of polyethylene glycol (150 gram, 0.75 mole) in DMA (500 ml) was added sodium hydride (30 gram, 60% in mineral oil) slowly at 0° C. for 24 hours. The resin was subsequently washed with 2×1:1 DMF-$H_2O$, 2×DMF, 3×5% HCl/$H_2O$, 3×$H_2O$, 2×MeOH, 3×DCM, and dried over high vacuum overnight. The substitution on the resin was over 96% determined by element analysis of chlorine composition.

EXAMPLE 3

The hydroxyl group of the short-chain PEG linker resin of Example 2 was acylated with excess phthalic anhydride (4 equiv.) and triethylamine in N, N-dimethylacetamide (DMA). This step immobilizes the phthalate to the solid support, and also generates the corresponding monoester and carboxylic acid (i.e., compound 6 of FIG. 5) for further manipulations. The immobilized carboxylic acid moiety was converted to an acyl azide using DPPA (4 equiv.) and TEA in toluene at room temperature in two hours. This procedure was found to be a more efficient for introducing the acyl azide group on the solid phase than the traditional combination of an acid chloride with $NaN_3$. The corresponding acyl azide was transformed to isocyanate 7 by heating in toluene at 90° C. for 4 hours. This transformation was monitored using FT-IR: when the acyl azide was formed, the corresponding absorption peak (2135 $cm^{-1}$) was observed in diffuse reflectance analysis of FT-IR. As the Curtius rearrangement occurred, a new peak corresponding to the aromatic isocyanate (2260 $cm^{-1}$) was intensified.

The formation of ureas 8 was straightforward by treatment of isocyanate with primary amines (4 equiv.) on the synthesizer. The isocyanate on resin was prepared on a large scale in a peptide synthesis vessel. Then this resin (80 mg resin to each well) was transferred to 96-well reaction block in the ACT 496 synthesizer. The resin was resuspended in DMA (2 ml) with the primary amine (50 mg in each well) for 4 hours. Then the resin was washed and mixed with pre-ground $K_2CO_3$ powder (50 mg to each well) in acetonitrile (1.5 ml) for cyclization at 60° C. for 24 hours. DCM (1 ml) was added to each well at room temperature and the resulting solution was collected by filtration under pressure. The crude product was obtained from concentration and analyzed by LC-MS directly. The yields were calculated based on the nitrogen composition of isocyanate on resin by element analysis.

Figure 7:
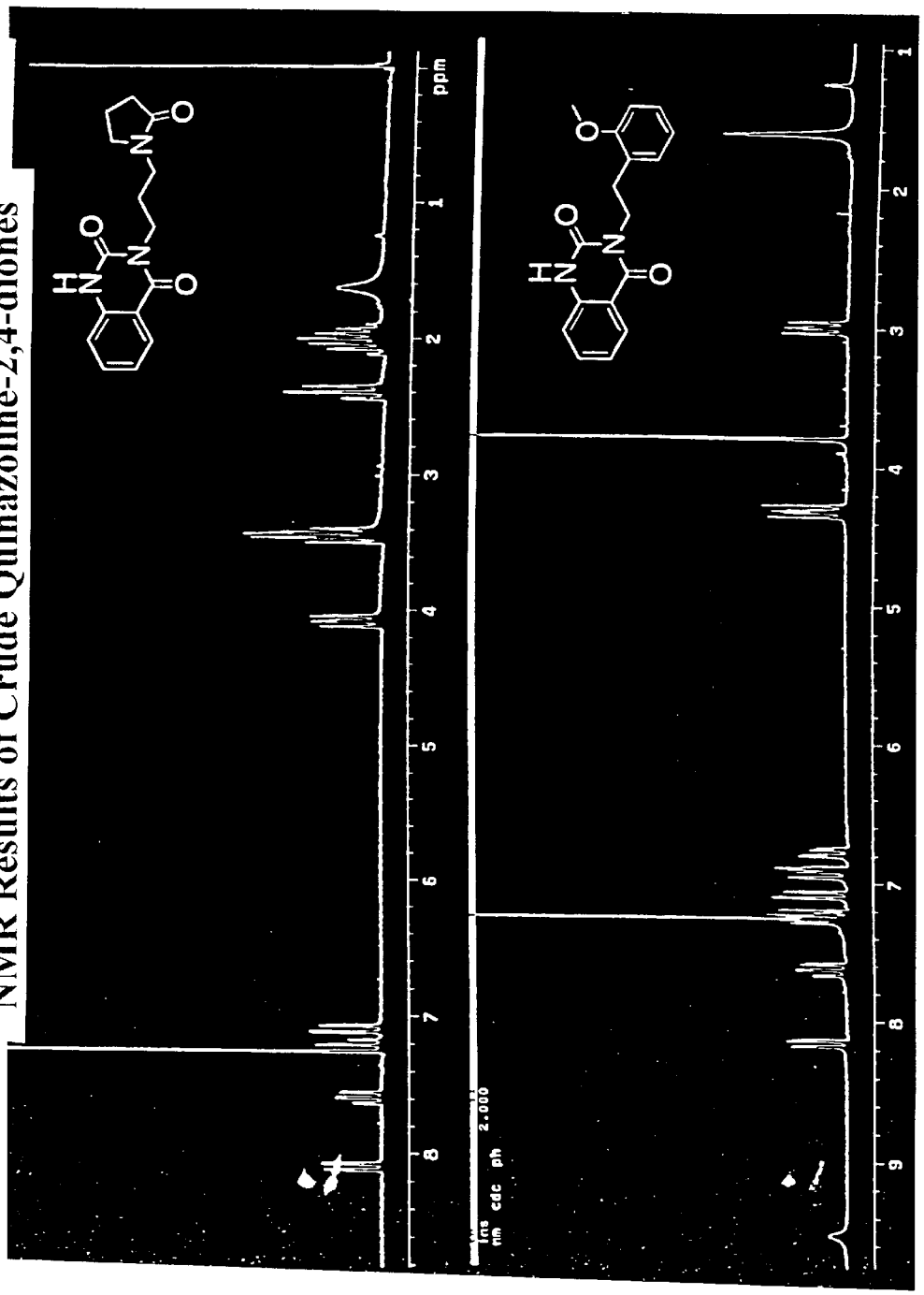
FIG. 7 depicts $^1$H NMR results of crude quinazoline-2,4-diones.
Figure 8:
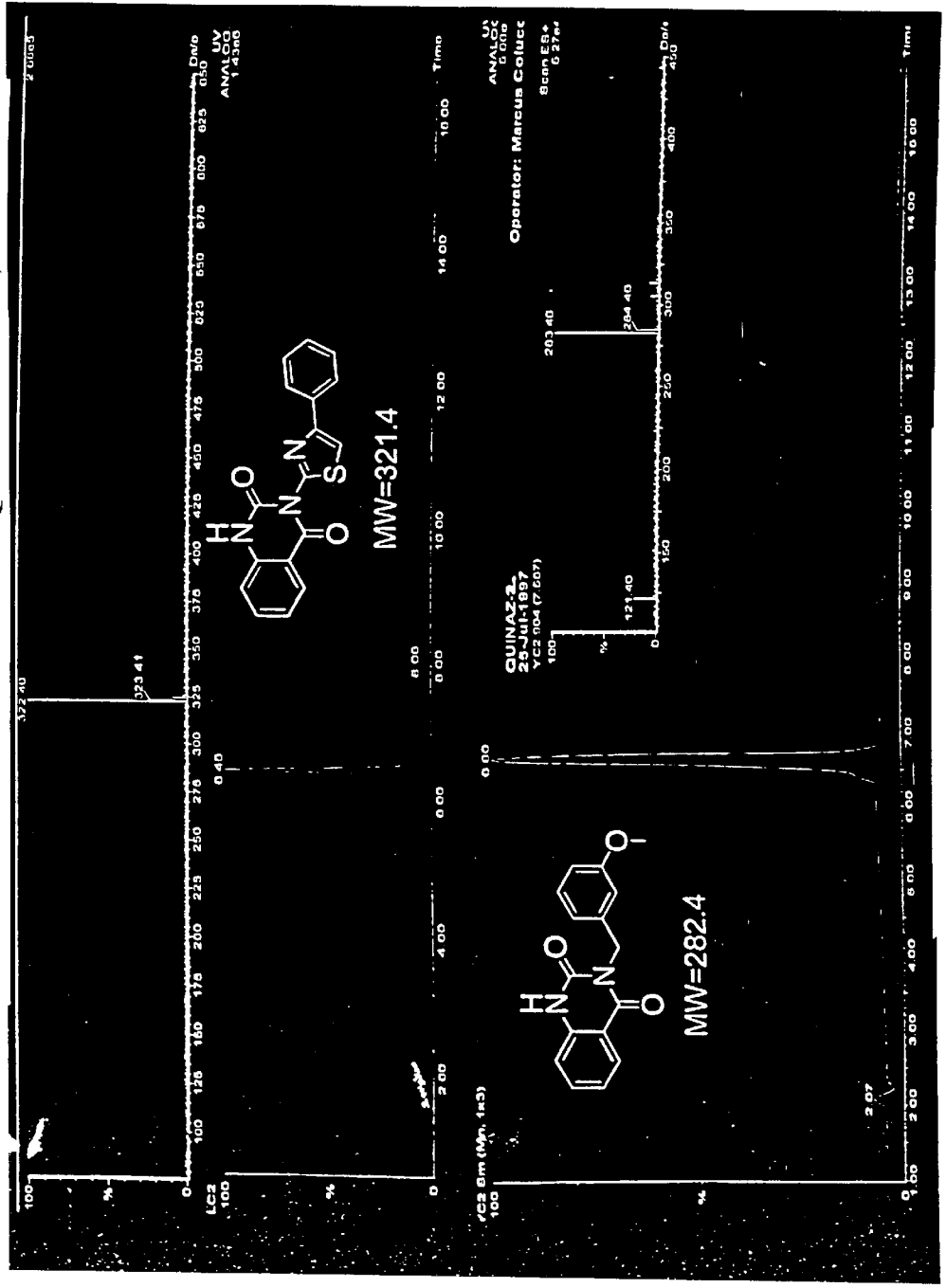
FIG. 8 depicts LC-MS results of crude quinazoline-2,4-diones.
Figure 9:
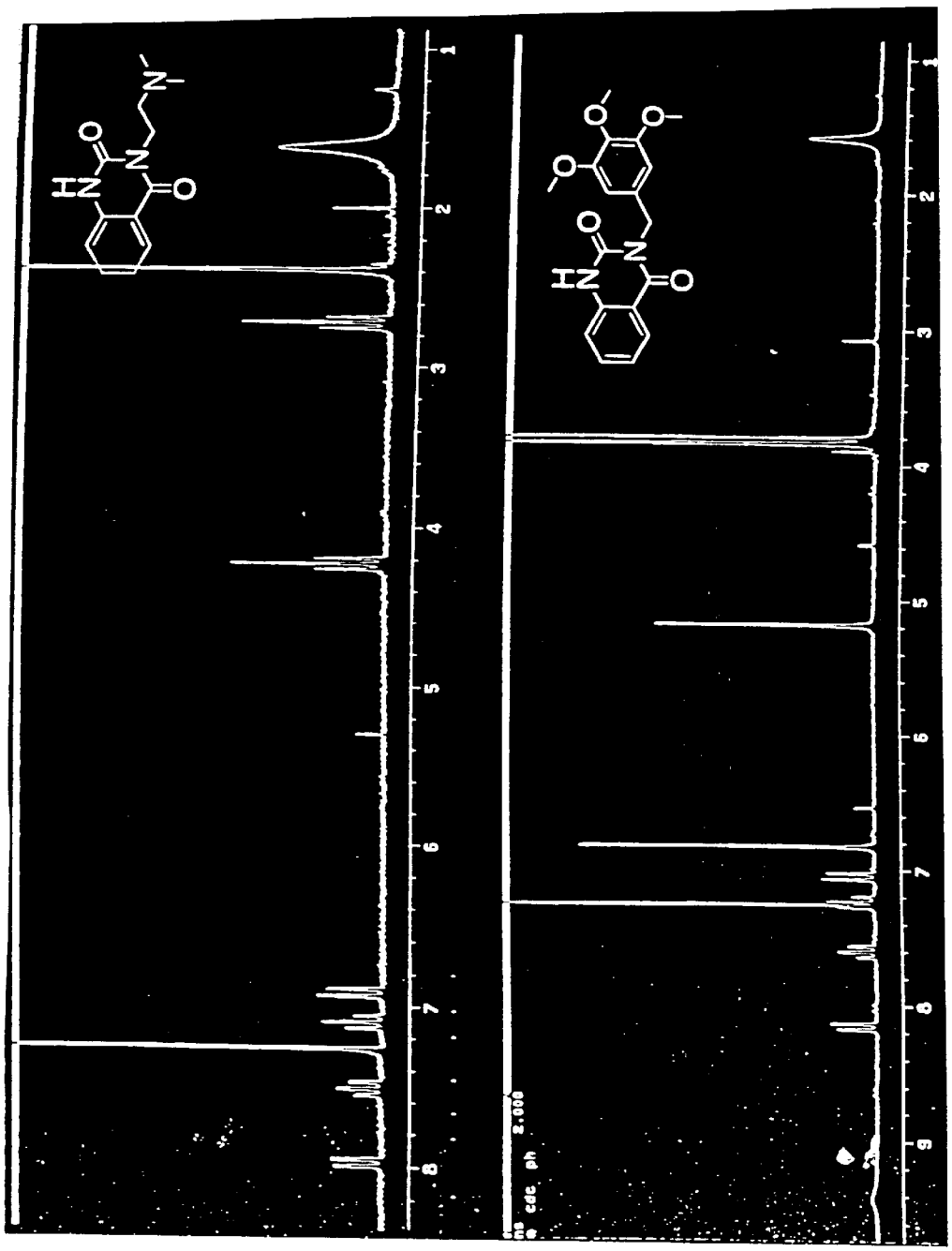
FIG. 9 depicts $^1$H NMR results of crude quinazoline-2,4-diones.
Figure 10:
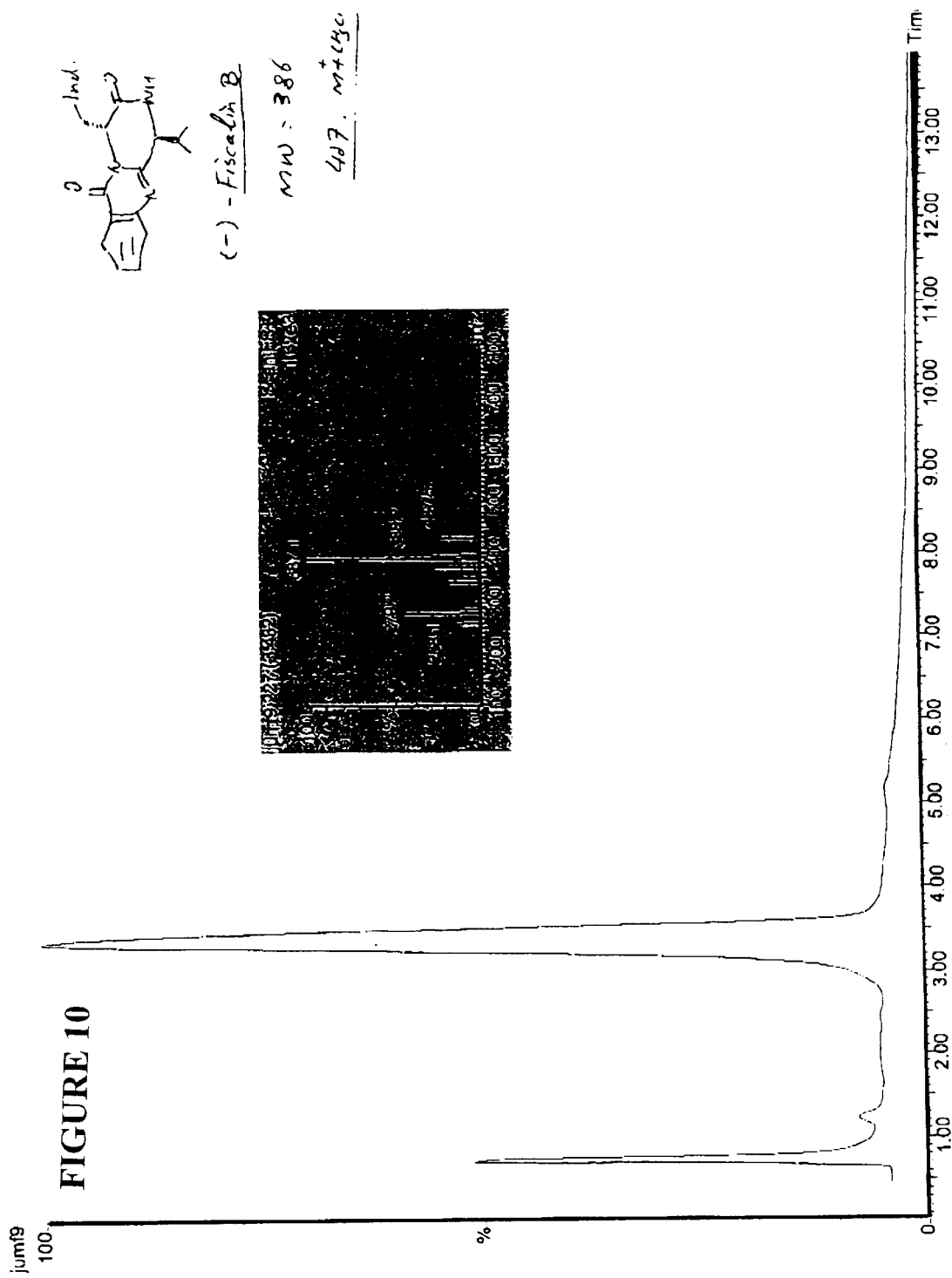
FIG. 10 depicts LC-MS results of (−) fiscalin B prepared by the method of the invention.

Under the conditions discussed above, the corresponding quinazoline-2, 4-diones 4 were generated in acetonitrile (1.5 ml in each well) with $K_2CO_3$ at 60° C. The cyclization was completed with 24 hours and methylene chloride (1 ml) was added to each well in order to precipitate trace amount of $K_2CO_3$ dissolved in acetonitrile. The solution of crude product was subject to analytical LC-MS. Because no organic base was involved in the final step and only the correct urea intermediate could cyclize and thereby be released from solid support, most products have excellent purity (over 90%) with good yield (over 70%) as shown in Table 1 (FIG. 6). FIGS. 7 through 9 depict representative $^1$H NMR and LC-MS results of crude quinazoline-2, 4-diones prepared by the methods of the invention. Additionally, FIG. 10 depicts a LC and MS of one of the quinazoline alkaloid described by Wang and Ganesan (H. Wang and A. Ganesan, *J Org. Chem.* 1998, 63, 2432), (−) Fiscalin B, prepared by the method of the invention. Synthesis of fumiquinazoline G and fumiquinazoline D can also be accomplished by the solid-phase synthesis methods of the invention as outlined above.

EXAMPLE 4

Figure 11:
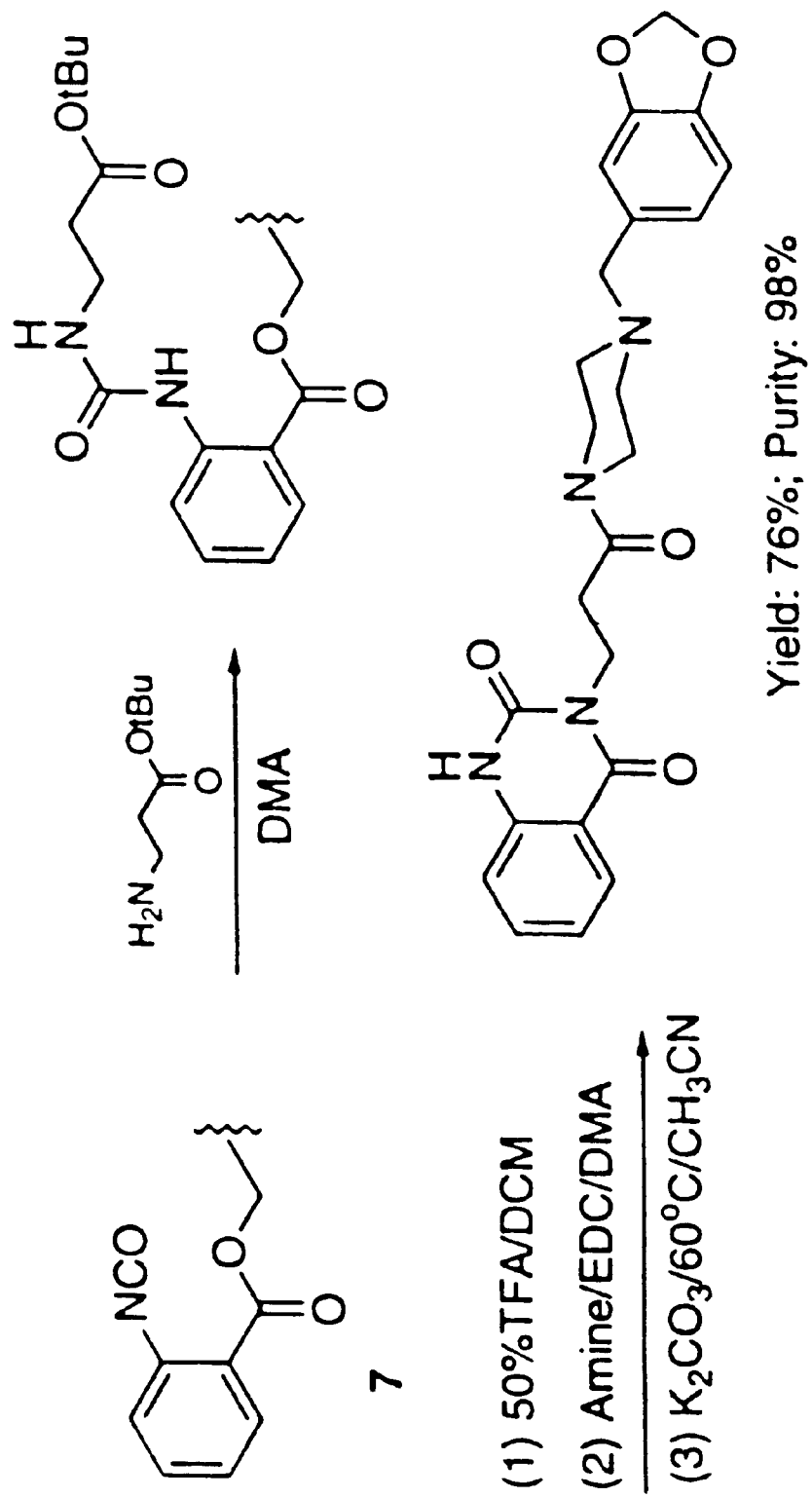
FIG. 11 shows a synthesis of a substituted quinazoline-2,4-dione.
Figure 12:
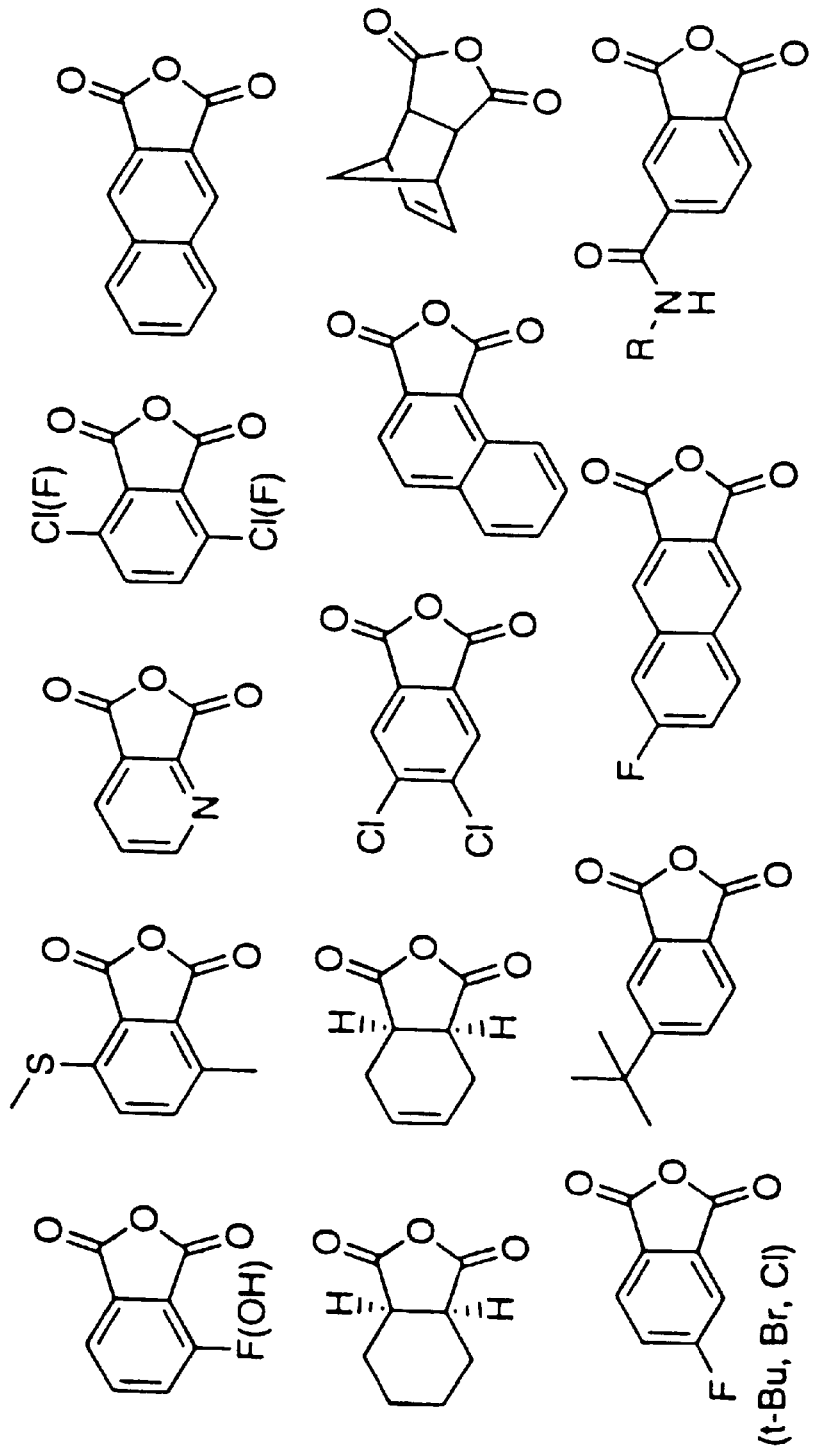
FIG. 12 depicts the structures of several commercially-available anhydrides.

To explore the molecular diversity of this library, primary amines with other functional groups can be introduced and diversified before cyclization and release of the quinazoline-2, 4-dione products. For example, as shown in FIG. 11, amino acids can react with isocyanate 7 to produce ureas. Then the carboxylic acid group of the amino acid can be unblocked and diversified by coupling with a variety of amines. There are approximately 40 commercially available analogs of phthalic anhydrides suitable for solid phase synthesis (FIG. 12). Still greater structural diversity can be achieved by reaction with a variety of amino acids and primary amines as described above.

EXAMPLE 5

Figure 13:
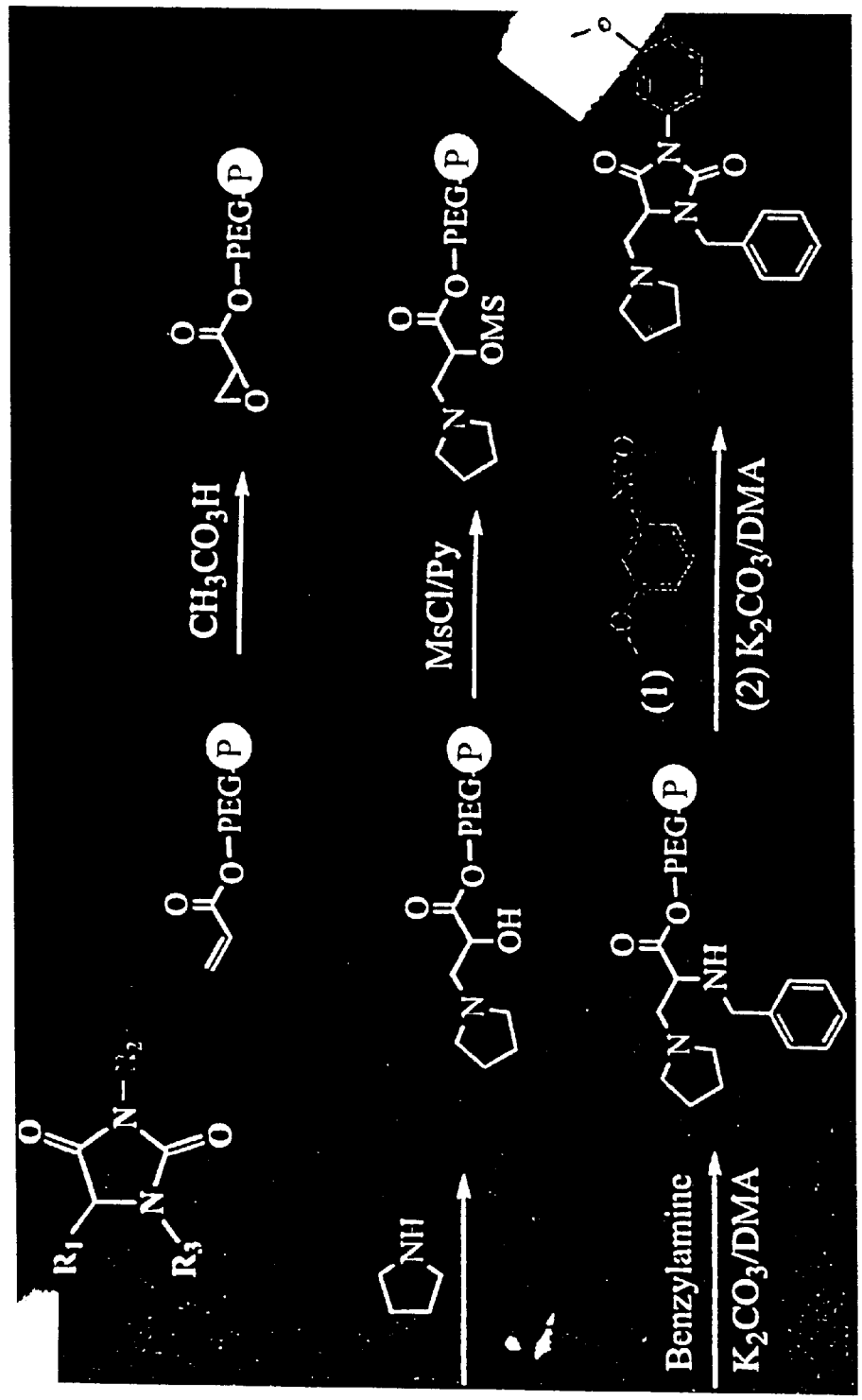
FIG. 13 shows a solid-phase synthesis of multiple substituted hydantoins under mild conditions.
Figure 14:
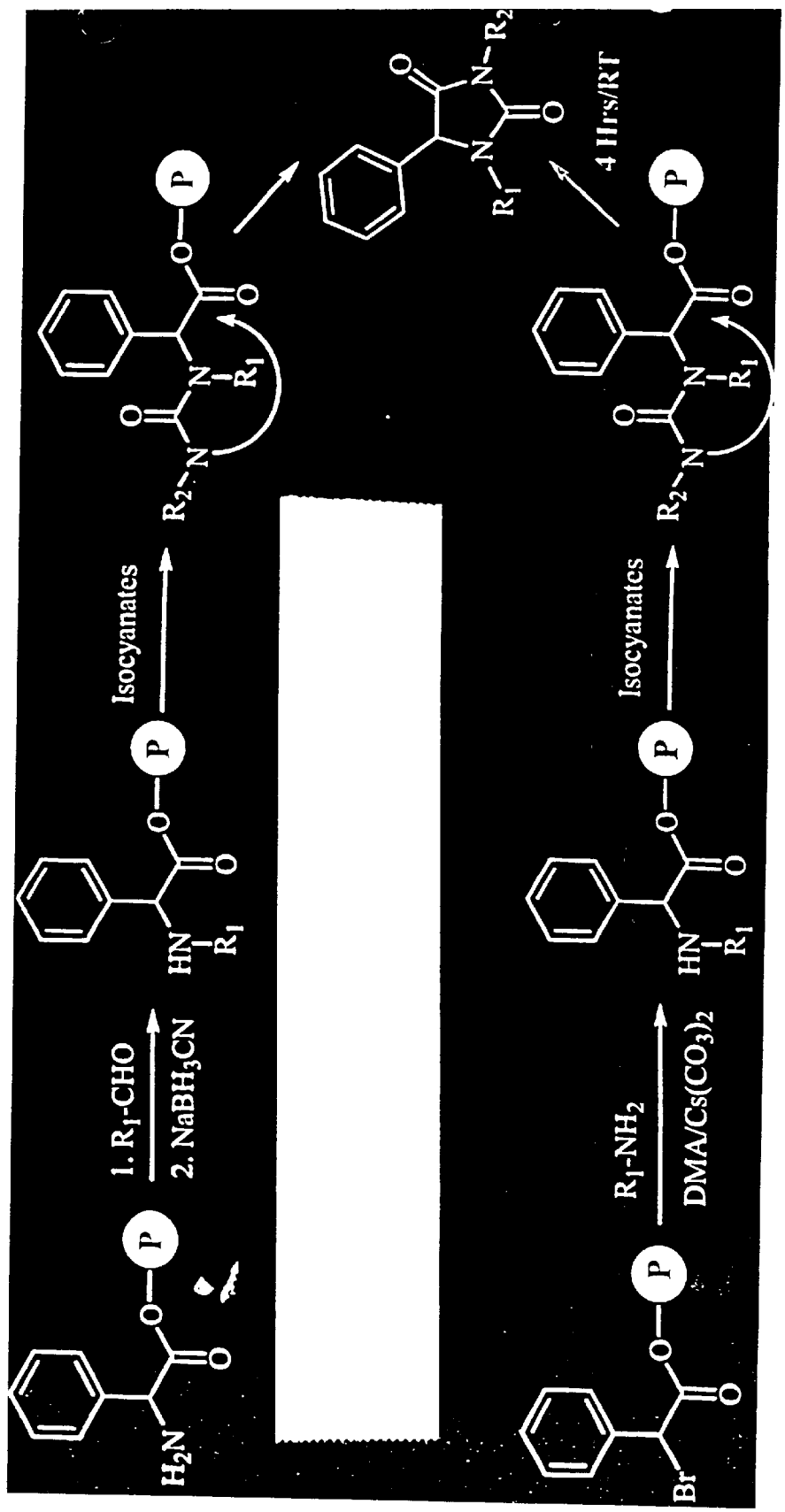
FIG. 14 shows a reaction sequence in the solid phase cyclization of hydantoins.
Figure 15:
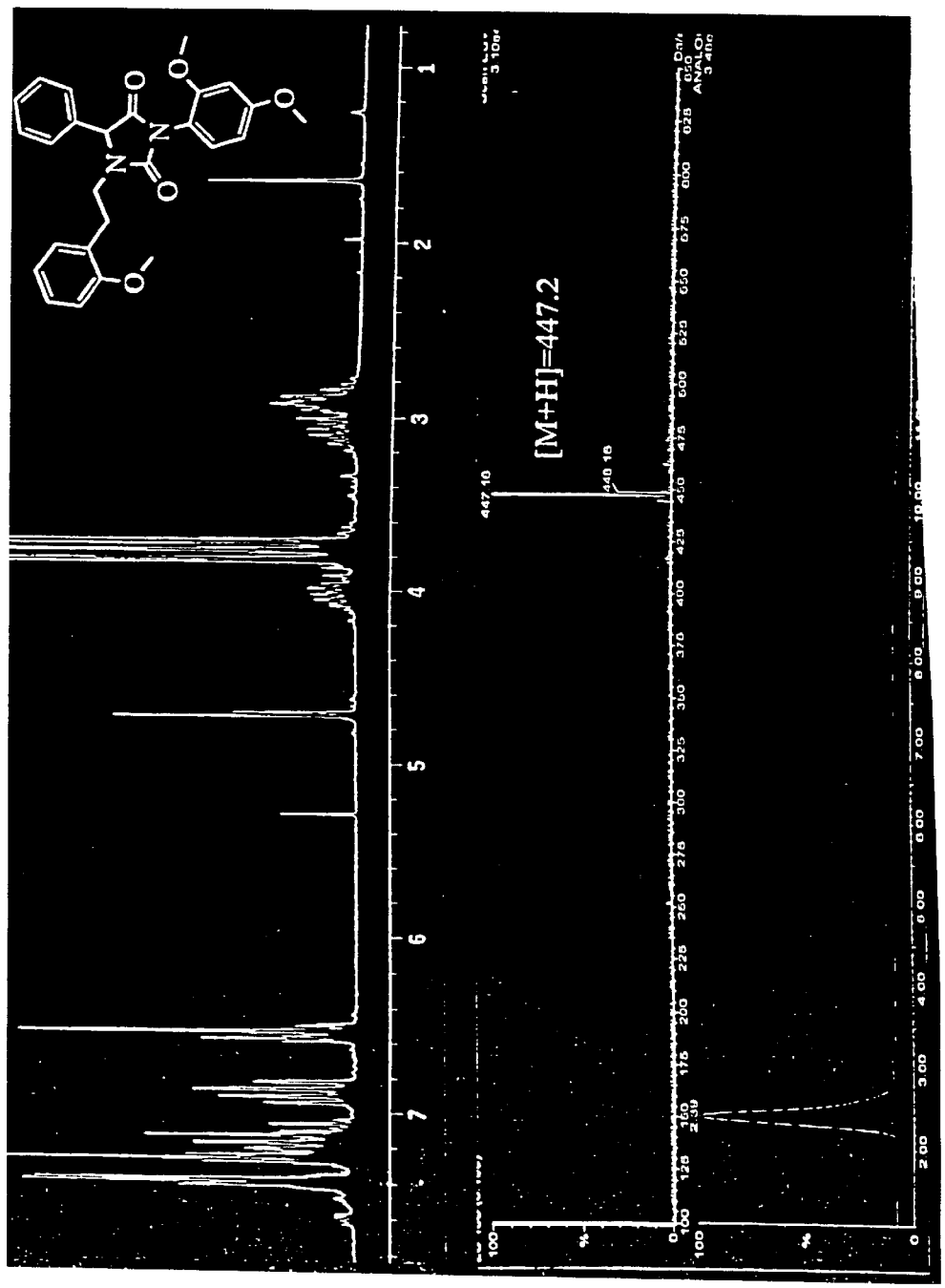
FIG. 15 is a $^1$H NMR and MS of a substituted hydantoin analog.

The synthesis described herein differs from previously-reported methods. Starting from an alpha-halo-carboxylic ester immobilized on short chain $PEG_4$-PS resin (e.g., prepared as in Example 2, supra), the alpha-halo group was replaced (by nucleophilic substitution at the reactive alpha-carbon) by a primary amine to form a secondary amine. Then an isocyanate was reacted with the secondary amine to form a urea. Under mild conditions ($K_2CO_3$ in acetonitrile at room temperature), the hydantoin was formed via a cyclization-cleavage reaction. (See for example, FIGS. 13 through 15 which depict a general synthesis, $^1$H NMR and MS of substituted hydantoins via treatment of an α, β acid on a solid support with a peracid followed by treatment with amines in the presence of a mild base, e.g., $M_nCO_3$, e.g., $K_2CO_3$, according to an embodiment of the present invention.)

Thus, alpha-bromo-phenylacetate, immobilized on short chain $PEG_4$-PS resin (1 gram, loading capacity=0.8 mmol/g) was treated with 2-methoxyphenethylamine (0.5 gram) and $K_2CO_3$ (0.3 gram, powder) in anhydrous DMA (15 ml) at room temperature for 6 hours. Then the resin was washed with different solvents to remove excess reagents and dried over high vacuum.

100 mg of the functionalized resin was then mixed with 60 mg 2,4-dimethoxyphenylsiocyanate (60 mg) in dimethylacetamide (1 ml) and shaken for 6 hours. Then the resin was washed with different solvents and mixed with $K_2CO_3$(50 mg) in acetonitrile (1.6 ml). The mixture was suspended in the shaker for 4 hours and the solution was collected and concentrated under reduced pressure. The desired crude product was 25 mg and purity was found to be over 90% based on LC-MS analysis.

There are over 30 alpha-halo-carboxylic acids and many primary amines commercially available (See, for example, FIG. 16). Thus, combinatorial library synthesis is readily accomplished by methods well known to the ordinarily skilled artisan.

As described herein, the present inventors have developed, inter alia, new methods and compounds useful for the construction of pyrimidine-2,4-diones, e.g., quinazoline-2, 4-diones, including combinatorial libraries thereof. Some key features in the methods include a short-chain PEG-PS support to provide a hydrophilic environment, efficient acyl azide formation on solid phase, Curtius rearrangement on the solid support, and a cyclo-cleavage reaction as the final step to ensure the purity of final product. In addition, using $K_2CO_3$ under mild temperatures to facilitate cyclization, instead of previously-reported organic bases, is a reliable and simple method, which should be applicable in other solid phase organic synthesis.

Those skilled in the art will recognize, or be able to ascertain using no more than routine experimentation, numerous equivalents to the specific procedures described herein. Such equivalents are considered to be within the scope of this invention and are covered by the following claims.

The contents of all publications and patent applications cited herein, including those in the background section, are hereby incorporated by reference.

Other embodiments are within the following claims.

What is claimed is:

1. A method for preparing a compound represented the formula (Formula I):

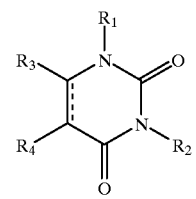

in which
the dashed line represents an optional bond;
$R_1$ and $R_2$ are each, independently, hydrogen, alkyl, or aryl;
$R_3$ and $R_4$ are each, independently, hydrogen, halogen, alkyl, or aryl; or $R_3$ and $R_4$ are joined to form a carbocyclic or heterocyclic ring having from 5 to 7 atoms in the ring moiety, wherein the atoms are selected from carbon, nitrogen, oxygen, or sulfur;
the method comprising:

reacting a compound represented by the formula (Formula II):

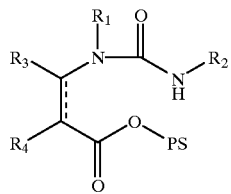

in which $R_1$, $R_2$, $R_3$, and $R_4$ are as described above, and PS is a polymer support, by;

contacting the compound represented by Formula II with a solid inorganic base in an amount sufficient to promote ring closure and cleavage from the polymer support under conditions such that the compound of Formula I is prepared.

2. The method of claim 1, wherein the step of reacting the compound of Formula II under conditions such that the compound of Formula I is formed comprises contacting the compound of Formula II with an effective ring-closing amount of $M_nCO_3$, in which M is an alkali metal or an alkaline earth metal, and n is 1 or 2.

3. The method of claim 1, wherein the compound of Formula I is represented by the formula (Formula III):

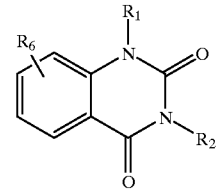

in which $R_6$ represents zero to four substituents each independently selected from the group consisting of halogen, hydroxy, alkoxy, alkyl, aryl, mercapto, and alkylthio.

4. The method of claim 1, wherein PS is —(CH$_2$CH$_2$O)$_m$-polymer, in which m is an integer between 3 and 5, and polymer is a methylbenzene-divinylbenzene copolymer.

* * * * *